(12) United States Patent
Radwan et al.

(10) Patent No.: US 12,145,930 B1
(45) Date of Patent: Nov. 19, 2024

(54) 4-THIAZOLIDINONE DERIVATIVES AS EGFR INHIBITORS FOR ANTI-TUMOR ACTIVITY

(71) Applicant: KING FAISAL UNIVERSITY, Al-Ahsa (SA)

(72) Inventors: Ibrahim Taha Radwan, Al-Ahsa (SA); Mohamed Marzok, Al-Ahsa (SA); Adel Alsheikh Mubarek, Al-Ahsa (SA); Abdelfatah Seleim, Al-Ahsa (SA)

(73) Assignee: KING FAISAL UNIVERSITY, Al-Ahsa (SA)

( * ) Notice: Subject to any disclaimer, the term of this patent is extended or adjusted under 35 U.S.C. 154(b) by 0 days.

(21) Appl. No.: 18/443,136

(22) Filed: Feb. 15, 2024

(51) Int. Cl.
| | |
|---|---|
| *C07D 417/12* | (2006.01) |
| *A61K 9/51* | (2006.01) |
| *A61K 31/426* | (2006.01) |
| *A61K 31/427* | (2006.01) |
| *A61P 35/00* | (2006.01) |
| *C07D 277/54* | (2006.01) |
| *C07D 417/06* | (2006.01) |

(52) U.S. Cl.
CPC .......... *C07D 417/12* (2013.01); *A61K 9/5123* (2013.01); *A61K 9/5161* (2013.01); *A61K 31/426* (2013.01); *A61K 31/427* (2013.01); *A61P 35/00* (2018.01); *C07D 277/54* (2013.01); *C07D 417/06* (2013.01)

(58) Field of Classification Search
None
See application file for complete search history.

(56) References Cited

PUBLICATIONS

Baell et al., "New Substructure Filers for Removal of Pan Assay Interference Compounds (PAINS) from Screening Libraries and for Their Exclusion in Bioassays", J. Med. Chem. Feb. 4, 2010 (Year: 2010).*
PubChem Applicant's compound (3) PA0001504.
PubChem 2-Hydroxy-5-phenylazobenzaldehyde compound 8a PA0001504.
PubChem 2-hydroxy-5-((4-methoxyphenyl)diazenyl)benzaldehyde compound 8b PA0001504.
Agnieszka Gornowicz et al; "Multi-Targeting Anticancer Activity of a New 4-Thiazolidinone Derivative with Anti-HER2 Antibodies in Human AGS Gastric Cancer Cells"; Int J Mol Sci. Apr. 2023; 24(7): 6791. Published online Apr. 5, 2023. doi: 10.3390/ijms24076791.
Piotr Roszczeńko et al; "4-Thiazolidinone-Bearing Hybrid Molecules in Anticancer Drug Design"; Int J Mol Sci. Nov. 2022; 23(21): 13135. Published online Oct. 28, 2022. doi: 10.3390/ijms232113135.
Bartosz Skóra et al; "Evaluation of Anticancer and Antibacterial Activity of Four 4-Thiazolidinone-Based Derivatives"; Molecules 2022, 27(3), 894; https://doi.org/10.3390/molecules27030894.
Dipanjan Pan et al; "A strategy for combating melanoma with oncogenic c-Myc inhibitors and targeted nanotherapy"; Nanomedicine (Lond). Jan. 2015; 10(2): 241-251. doi: 10.2217/nnm.14.101.

* cited by examiner

*Primary Examiner* — Andrew D Kosar
*Assistant Examiner* — Gillian A Hutter
(74) *Attorney, Agent, or Firm* — Nath, Goldberg & Meyer; Joshua B. Goldberg

(57) ABSTRACT

Novel heterocyclic 4-thiazolidinone conjugates, a method of synthesizing said compounds, a pharmaceutical composition comprising said compounds and a suitable carrier, and a method of using the compounds. The heterocyclic 4-thiazolidinone conjugates, identified as EGFR inhibitors, are useful as anticancer and/or antitumor agents.

19 Claims, No Drawings

4-THIAZOLIDINONE DERIVATIVES AS EGFR INHIBITORS FOR ANTI-TUMOR ACTIVITY

BACKGROUND

1. Field

The present disclosure provides novel heterocyclic 4-thiazolidinone conjugates as novel epidermal growth factor receptor (EGFR) inhibitors that slow down cell growth by binding to certain parts of the EGFR protein, compositions containing such compounds, and methods of their preparation. These compounds and compositions are useful as therapeutic agents for treating proliferative disorders such as cancer.

2. Description of the Related Art

The requirements of antitumor therapeutics call for constant development of new anticancer agents with the aim of generating medicaments that are more potent and well tolerated.

Thus, new antitumoral/anti-cancer compounds solving the aforementioned problems are desired.

SUMMARY

The present subject matter relates to the use of 4-thiazolidinone derivatives as EGFR inhibitors with improved potential for treating various types of cancer. The requirements of antitumor therapeutics call for constant development of new anticancer agents with the aim of generating medicaments that are more potent and well tolerated.

The presently described compounds are not only new but have very valuable antitumoral properties. The compounds were tested for their cytotoxicity against three human tumor cell lines of a human prostate cancer cell line ($PC_3$), colorectal carcinoma colon cancer (HCT-116), and human breast cancer (MCF7). The results showed strong anti-tumor activity.

In an embodiment, the present subject matter relates to a compound having the formula I:

or a pharmaceutically acceptable salt, ester, stereoisomer, or solvate thereof, wherein:
R is selected from the group consisting of hydrogen; an optionally substituted CHAr substituted with one or more substituents independently selected from the group consisting of hydrogen, hydroxy, methoxy, a halogen, naphthalene, a 1H-indol-3-yl, and a dimethyl amino; 2-hydroxy-5-((E)-phenyldiazenyl)benzylidene; 2-hydroxy-5((4 methoxyphenyl)diazinyl)benzylidene; 5-((4-chlorophenyl)-2-hydroxybenzylidene); and (dimethylamino)methylene.

In another embodiment, the present subject matter relates to a compound having the formula I:

or a pharmaceutically acceptable salt, ester, stereoisomer, or solvate thereof, wherein:
R is selected from the group consisting of hydrogen, a —CHphenyl substituted with one or more substituents independently selected from the group consisting of hydrogen, hydroxy, methoxy, chlorine, naphthalene, 1H-indol-3-yl, and dimethyl amino; 2-hydroxy-5-((E)-phenyldiazenyl)benzylidene; 2-hydroxy-5((4-methoxyphenyl)diazinyl)benzylidene; 5-((4-chlorophenyl)-2-hydroxybenzylidene); and (dimethylamino) methylene.

In an embodiment, the present subject matter relates to a compound selected from the group consisting of: 4-((3-benzoyl-4-oxothiazolidin-2-ylidene)amino)benzoic acid (4); 4((3-benzoyl-5-(benzylidene)-4-oxothiazolidin-2-ylidene) amino)benzoic acid (6a); 4-((3-benzoyl-5-(4-hydroxybenzylidene)-4-oxothiazolidin-2-ylidene)amino)benzoic acid (6b); 4-((3-benzoyl-5-(2,4-dihydroxybenzylidene)-4-oxothiazolidin-2-ylidene)amino) benzoic acid (6c); 4-((3-benzoyl-5-(4-methoxybenzylidene)-4-oxothiazolidin-2-ylidene)amino) benzoic acid (6d); 4-((3-benzoyl-5-(3,5-dimethoxybenzylidene)-4-oxothiazolidin-2-ylidene)amino) benzoic acid (6e); 4((3-benzoyl-5-(3,5-dichlorobenzylidene)-4-oxothiazolidin-2-ylidene)amino) benzoic acid (6f); 4-((3-benzoyl-5-(naphthalen-2-ylmethylene)-4-oxothiazolidin-2-ylidene)amino) benzoic acid (6g); 4-((5-((1H-indol-3-yl)methylene)-3-benzoyl-4-oxothiazolidin-2-ylidene)amino) benzoic acid (6h); 4-((3-benzoyl-5-(4 (dimethylamino)benzylidene)-4-oxothiazolidin-2-ylidene) amino) benzoic acid (6i); 4-((3-benzoyl-5-(2-hydroxy-5-((E)-phenyldiazenyl)benzylidene)-4-oxothiazolidin-2-ylidene)amino) benzoic acid (9a); 4-((3-benzoyl-5-(2-hydroxy-5-((4 methoxyphenyl)diazenyl)benzylidene)-4-oxothiazolidin-2-ylidene)amino)benzoic acid (9b); 4-((3-benzoyl-5-(5-((4-chlorophenyl)diazenyl)-2-hydroxybenzylidene)-4-oxothiazolidin-2-ylidene)amino) benzoic acid (9c); 4-((3-benzoyl-5-((dimethylamino) methylene)-4-oxothiazolidin-2-ylidene)amino) benzoic acid (10); 4-(5-(((1H-1,2,4-triazol-3-yl)amino) methylene)-3-benzoyl-4-oxothiazolidin-2-ylidene)amino)benzoic acid (11); and a pharmaceutically acceptable salt, ester, stereoisomer, or solvate thereof.

In an embodiment, the present subject matter relates to a process for the synthesis of the compounds of formula I, including a number of species or specific structures falling under structural formula I. Further contemplated herein are pharmaceutical compositions containing these compounds, as well as methods of inhibiting epidermal growth factor receptor (EGFR) activity and of treating various cancers by administering the present compounds to a patient in need thereof.

These and other features of the present subject matter will become readily apparent upon further review of the following specification.

DETAILED DESCRIPTION OF THE PREFERRED EMBODIMENTS

The following definitions are provided for the purpose of understanding the present subject matter and for construing the appended patent claims.

Definitions

Throughout the application, where compositions are described as having, including, or comprising specific components, or where processes are described as having, including, or comprising specific process steps, it is contemplated that compositions of the present teachings can also consist essentially of, or consist of, the recited components, and that the processes of the present teachings can also consist essentially of, or consist of, the recited process steps.

It is noted that, as used in this specification and the appended claims, the singular forms "a", "an", and "the" include plural references unless the context clearly dictates otherwise.

In the application, where an element or component is said to be included in and/or selected from a list of recited elements or components, it should be understood that the element or component can be any one of the recited elements or components, or the element or component can be selected from a group consisting of two or more of the recited elements or components. Further, it should be understood that elements and/or features of a composition or a method described herein can be combined in a variety of ways without departing from the spirit and scope of the present teachings, whether explicit or implicit herein.

The use of the terms "include," "includes", "including," "have," "has," or "having" should be generally understood as open-ended and non-limiting unless specifically stated otherwise.

The use of the singular herein includes the plural (and vice versa) unless specifically stated otherwise. In addition, where the use of the term "about" is before a quantitative value, the present teachings also include the specific quantitative value itself, unless specifically stated otherwise. As used herein, the term "about" refers to a ±10% variation from the nominal value unless otherwise indicated or inferred.

As used herein, "halo" or "halogen" refers to fluoro, chloro, bromo, and iodo.

As used herein, "alkyl" refers to a straight-chain or branched saturated hydrocarbon group. Examples of alkyl groups include methyl (Me), ethyl (Et), propyl (e.g., n-propyl and z'-propyl), butyl (e.g., n-butyl, z'-butyl, sec-butyl, tert-butyl), pentyl groups (e.g., n-pentyl, z'-pentyl, -pentyl), hexyl groups, and the like. In various embodiments, an alkyl group can have 1 to 40 carbon atoms (i.e., $C_1$-$C_{40}$ alkyl group), for example, 1-30 carbon atoms (i.e., $C_1$-$C_{30}$ alkyl group). In some embodiments, an alkyl group can have 1 to 6 carbon atoms, and can be referred to as a "lower alkyl group" or a "$C_1$-$C_6$ alkyl group". Examples of lower alkyl groups include methyl, ethyl, propyl (e.g., n-propyl and z'-propyl), and butyl groups (e.g., n-butyl, z'-butyl, sec-butyl, tert-butyl). In some embodiments, alkyl groups can be substituted as described herein. An alkyl group is generally not substituted with another alkyl group, an alkenyl group, or an alkynyl group.

As used herein, "alkenyl" refers to a straight-chain or branched alkyl group having one or more carbon-carbon double bonds. Examples of alkenyl groups include ethenyl, propenyl, butenyl, pentenyl, hexenyl, butadienyl, pentadienyl, hexadienyl groups, and the like. The one or more carbon-carbon double bonds can be internal (such as in 2-butene) or terminal (such as in 1-butene). In various embodiments, an alkenyl group can have 2 to 40 carbon atoms (i.e., $C_2$-$C_{40}$ alkenyl group), for example, 2 to 20 carbon atoms (i.e., $C_2$-$C_{20}$ alkenyl group) or 2 to 6 carbon atoms (i.e., $C_2$-$C_6$ alkenyl group). In some embodiments, alkenyl groups can be substituted as described herein. An alkenyl group is generally not substituted with another alkenyl group, an alkyl group, or an alkynyl group.

The term "substituted alkyl" as used herein refers to an alkyl group in which 1 or more (up to about 5, for example about 3) hydrogen atoms is replaced by a substituent independently selected from the group: —O, —S, acyl, acyloxy, optionally substituted alkoxy, optionally substituted amino (wherein the amino group may be a cyclic amine), azido, carboxyl, (optionally substituted alkoxy)carbonyl, amido, cyano, optionally substituted cycloalkyl, optionally substituted cycloalkenyl, halogen, hydroxyl, nitro, sulfamoyl, sulfanyl, sulfinyl, sulfonyl, and sulfonic acid. Some of the optional substituents for alkyl are hydroxy, halogen exemplified by chloro and bromo, acyl exemplified by methylcarbonyl; alkoxy, and heterocyclyl exemplified by morpholino and piperidino. Other alkyl substituents as described herein may further be contemplated.

The term "substituted alkenyl" refers to an alkenyl group in which 1 or more (up to about 5, for example about 3) hydrogen atoms is replaced by a substituent independently selected from those listed above with respect to a substituted alkyl. Other alkenyl substituents as described herein may further be contemplated.

As used herein, "heteroatom" refers to an atom of any element other than carbon or hydrogen and includes, for example, nitrogen, oxygen, silicon, sulfur, phosphorus, and selenium.

As used herein, "aryl" refers to an aromatic monocyclic hydrocarbon ring system or a polycyclic ring system in which two or more aromatic hydrocarbon rings are fused (i.e., having a bond in common with) together or at least one aromatic monocyclic hydrocarbon ring is fused to one or more cycloalkyl and/or cycloheteroalkyl rings. An aryl group can have 6 to 24 carbon atoms in its ring system (e.g., $C_6$-$C_{24}$ aryl group), which can include multiple fused rings. In some embodiments, a polycyclic aryl group can have 8 to 24 carbon atoms. Any suitable ring position of the aryl group can be covalently linked to the defined chemical structure. Examples of aryl groups having only aromatic carbocyclic ring(s) include phenyl, 1-naphthyl (bicyclic), 2-naphthyl (bicyclic), anthracenyl (tricyclic), phenanthrenyl (tricyclic), pentacenyl (pentacyclic), and like groups. Examples of polycyclic ring systems in which at least one aromatic carbocyclic ring is fused to one or more cycloalkyl and/or cycloheteroalkyl rings include, among others, benzo derivatives of cyclopentane (i.e., an indanyl group, which is a 5,6-bicyclic cycloalkyl/aromatic ring system), cyclohexane (i.e., a tetrahydronaphthyl group, which is a 6,6-bicyclic cycloalkyl/aromatic ring system), imidazoline (i.e., a benzimidazolinyl group, which is a 5,6-bicyclic cycloheteroalkyl/aromatic ring system), and pyran (i.e., a chromenyl group, which is a 6,6-bicyclic cycloheteroalkyl/aromatic ring system). Other examples of aryl groups include benzodioxanyl, benzodioxolyl, chromanyl, indolinyl groups, and the like. In some embodiments, aryl groups can be substituted as described herein. In some embodiments, an aryl group can have one or more halogen substituents, and can be referred to as a "haloaryl" group. Perhaloaryl groups, i.e., aryl groups where all of the hydrogen atoms are replaced with halogen atoms (e.g., —C6F5), are included within the definition of "haloaryl". In certain embodiments, an aryl group is substituted with another aryl group and can be referred to as a biaryl group. Each of the aryl groups in the biaryl group can be substituted as disclosed herein.

As used herein, "heteroaryl" refers to an aromatic monocyclic ring system containing at least one ring heteroatom selected from oxygen (O), nitrogen (N), sulfur (S), silicon (Si), and selenium (Se) or a polycyclic ring system where at least one of the rings present in the ring system is aromatic and contains at least one ring heteroatom. Polycyclic heteroaryl groups include those having two or more heteroaryl rings fused together, as well as those having at least one monocyclic heteroaryl ring fused to one or more aromatic carbocyclic rings, non-aromatic carbocyclic rings, and/or non-aromatic cycloheteroalkyl rings. A heteroaryl group, as a whole, can have, for example, 5 to 24 ring atoms and contain 1-5 ring heteroatoms (i.e., 5-20 membered heteroaryl group). The heteroaryl group can be attached to the defined chemical structure at any heteroatom or carbon atom that results in a stable structure. Generally, heteroaryl rings do not contain O-13 O, S—S, or S—O bonds. However, one or more N or S atoms in a heteroaryl group can be oxidized (e.g., pyridine N-oxide thiophene S-oxide, thiophene S,S-dioxide). Examples of heteroaryl groups include, for example, the 5- or 6-membered monocyclic and 5-6 bicyclic ring systems shown below: where T is O, S, NH, N-alkyl, N-aryl, N-(arylalkyl) (e.g., N-benzyl), $SiH_2$, SiH(alkyl), Si(alkyl)$_2$, SiH(arylalkyl), Si(arylalkyl)$_2$, or Si(alkyl)(arylalkyl). Examples of such heteroaryl rings include pyrrolyl, furyl, thienyl, pyridyl, pyrimidyl, pyridazinyl, pyrazinyl, triazolyl, tetrazolyl, pyrazolyl, imidazolyl, isothiazolyl, thiazolyl, thiadiazolyl, isoxazolyl, oxazolyl, oxadiazolyl, indolyl, isoindolyl, benzofuryl, benzothienyl, quinolyl, 2-methylquinolyl, isoquinolyl, quinoxalyl, quinazolyl, benzotriazolyl, benzimidazolyl, benzothiazolyl, benzisothiazolyl, benzisoxazolyl, benzoxadiazolyl, benzoxazolyl, cinnolinyl, 1H-indazolyl, 2H-indazolyl, indolizinyl, isobenzofuyl, naphthyridinyl, phthalazinyl, pteridinyl, purinyl, oxazolopyridinyl, thiazolopyridinyl, imidazopyridinyl, furopyridinyl, thienopyridinyl, pyridopyrimidinyl, pyridopyrazinyl, pyridopyridazinyl, thienothiazolyl, thienoxazolyl, thienoimidazolyl groups, and the like. Further examples of heteroaryl groups include 4,5,6,7-tetrahydroindolyl, tetrahydroquinolinyl, benzothienopyridinyl, benzofuropyridinyl groups, and the like. In some embodiments, heteroaryl groups can be substituted as described herein.

The term "optional" or "optionally" means that the subsequently described event or circumstance may or may not occur, and that the description includes instances where said event or circumstance occurs and instances in which it does not. For example, "optionally substituted alkyl" means either "alkyl" or "substituted alkyl," as defined herein.

It will be understood by those skilled in the art with respect to any chemical group containing one or more substituents that such groups are not intended to introduce any substitution or substitution patterns that are sterically impractical and/or physically non-feasible.

The term "isomers" or "stereoisomers" as used herein relates to compounds that have identical molecular formulae but that differ in the arrangement of their atoms in space. Stereoisomers that are not mirror images of one another are termed "diastereoisomers" and stereoisomers that are non-superimposable mirror images are termed "enantiomers," or sometimes optical isomers. A carbon atom bonded to four non-identical substituents is termed a "chiral center." Certain compounds herein have one or more chiral centers and therefore may exist as either individual stereoisomers or as a mixture of stereoisomers. Configurations of stereoisomers that owe their existence to hindered rotation about double bonds are differentiated by their prefixes cis and trans (or Z and E), which indicate that the groups are on the same side (cis or Z) or on opposite sides (trans or E) of the double bond in the molecule according to the Cahn-Ingold-Prelog rules. All possible stereoisomers are contemplated herein as individual stereoisomers or as a mixture of stereoisomers.

Unless defined otherwise, all technical and scientific terms used herein have the same meaning as commonly understood to one of ordinary skill in the art to which the presently described subject matter pertains.

Where a range of values is provided, for example, concentration ranges, percentage ranges, or ratio ranges, it is understood that each intervening value, to the tenth of the unit of the lower limit, unless the context clearly dictates otherwise, between the upper and lower limit of that range and any other stated or intervening value in that stated range, is encompassed within the described subject matter. The upper and lower limits of these smaller ranges may independently be included in the smaller ranges, and such embodiments are also encompassed within the described subject matter, subject to any specifically excluded limit in the stated range. Where the stated range includes one or both of the limits, ranges excluding either or both of those included limits are also included in the described subject matter.

Throughout the application, descriptions of various embodiments use "comprising" language. However, it will be understood by one of skill in the art, that in some specific instances, an embodiment can alternatively be described using the language "consisting essentially of" or "consisting of".

"Subject" as used herein refers to any animal classified as a mammal, including humans, domestic and farm animals, and zoo, sports, and pet companion animals such as household pets and other domesticated animals such as, but not limited to, cattle, sheep, ferrets, swine, horses, poultry, rabbits, goats, dogs, cats and the like.

"Patient" as used herein refers to a subject in need of treatment of a condition, disorder, or disease, such as cancer.

For purposes of better understanding the present teachings and in no way limiting the scope of the teachings, unless otherwise indicated, all numbers expressing quantities, percentages or proportions, and other numerical values used in the specification and claims, are to be understood as being modified in all instances by the term "about". Accordingly, unless indicated to the contrary, the numerical parameters set forth in the following specification and attached claims are approximations that may vary depending upon the desired properties sought to be obtained. At the very least, each numerical parameter should at least be construed in light of the number of reported significant digits and by applying ordinary rounding techniques.

In an embodiment, the present subject matter relates to a compound having the formula I:

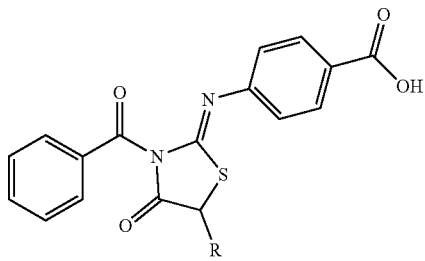

or a pharmaceutically acceptable salt, ester, stereoisomer, or solvate thereof, wherein:

R is selected from the group consisting of hydrogen; an optionally substituted CHAr substituted with one or more substituents independently selected from the group consisting of hydrogen, hydroxy, methoxy, a halogen, naphthalene, a 1H-indol-3-yl, and a dimethyl amino; 2-hydroxy-5-((E)-phenyldiazenyl)benzylidene; 2-hydroxy-5((4-methoxyphenyl)diazinyl)benzylidene; 5-((4-chlorophenyl)-2-hydroxybenzylidene); and (dimethylamino)methylene.

In another embodiment, the present subject matter relates to compounds of formula I, wherein R may be hydrogen.

In yet another embodiment, the present subject matter relates to compounds of formula I, wherein R is a —CHphenyl substituted with one or more substituents independently selected from the group consisting of one or more hydroxy groups, one or more methoxy groups, one or more halogens, a naphthalene, a 1H-indol-3-yl, and a dimethyl amino.

In still yet another embodiment, the present subject matter relates to a compound of formula I, wherein R is selected from the group consisting of 2-hydroxy-5-((E)-phenyldiazenyl)benzylidene; 2-hydroxy-5((4-methoxyphenyl)diazinyl)benzylidene; and 5-((4-chlorophenyl)-2-hydroxybenzylidene).

In another embodiment, the present subject matter relates to a compound having the formula I:

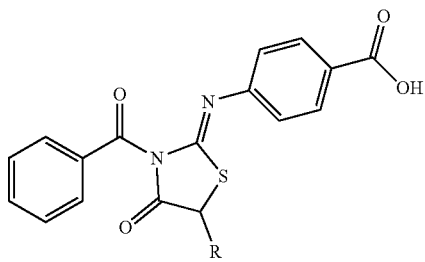

or a pharmaceutically acceptable salt, ester, stereoisomer, or solvate thereof, wherein:

R is selected from the group consisting of a hydrogen, a —CHphenyl substituted with one or more substituents independently selected from the group consisting of hydrogen, hydroxy, methoxy, chlorine, naphthalene, 1H-indol-3-yl, and dimethyl amino; 2-hydroxy-5-((E)-phenyldiazenyl)benzylidene; 2-hydroxy-5((4-methoxyphenyl)diazinyl)benzylidene; 5-((4-chlorophenyl)-2-hydroxybenzylidene); and (dimethylamino)methylene.

In an embodiment, the present subject matter relates to a compound selected from the group consisting of: 4-((3-benzoyl-4-oxothiazolidin-2-ylidene)amino)benzoic acid (4); 4-((3-benzoyl-5-(benzylidene)-4-oxothiazolidin-2-ylidene)amino)benzoic acid (6a); 4-((3-benzoyl-5-(4-hydroxybenzylidene)-4-oxothiazolidin-2-ylidene)amino)benzoic acid (6b); 4-((3-benzoyl-5-(2,4-dihydroxybenzylidene)-4-oxothiazolidin-2-ylidene) amino) benzoic acid (6c); 4((3-benzoyl-5-(4-methoxybenzylidene)-4-oxothiazolidin-2-ylidene)amino) benzoic acid (6d); 4-((3-benzoyl-5-(3,5-dimethoxybenzylidene)-4-oxothiazolidin-2-ylidene)amino) benzoic acid (6e); 4-((3-benzoyl-5-(3,5-dichlorobenzylidene)-4-oxothiazolidin-2-ylidene)amino) benzoic acid (6f); 4-((3-benzoyl-5-(naphthalen-2-ylmethylene)-4-oxothiazolidin-2-ylidene)amino) benzoic acid (6g); 4-((5-((1H-indol-3-yl)methylene)-3-benzoyl-4-oxothiazolidin-2-ylidene)amino) benzoic acid (6h); 4-((3-benzoyl-5-(4-(dimethylamino)benzylidene)-4-oxothiazolidin-2-ylidene) amino) benzoic acid (6i); 4-((3-benzoyl-5-(2-hydroxy-5-((E)-phenyldiazenyl)benzylidene)-4-oxothiazolidin-2-ylidene)amino) benzoic acid (9a); 4-((3-benzoyl-5-(2-hydroxy-5-((4-methoxyphenyl)diazenyl)benzylidene)-4-oxothiazolidin-2-ylidene)amino)benzoic acid (9b); 4-((3-benzoyl-5-(5-((4-chlorophenyl)diazenyl)-2-hydroxybenzylidene)-4-oxothiazolidin-2-ylidene)amino) benzoic acid (9c); 4-((3-benzoyl-5-((dimethylamino) methylene)-4-oxothiazolidin-2-ylidene)amino) benzoic acid (10); 4-(5-(((1H-1,2,4-triazol-3-yl)amino) methylene)-3-benzoyl-4-oxothiazolidin-2-ylidene)amino)benzoic acid (11); and a pharmaceutically acceptable salt, ester, stereoisomer, or solvate thereof.

Said differently, the present subject matter can relate to compounds of formula I selected from the group consisting of:

| No of novel compounds | Name according to scheme | structure | Scheme |
|---|---|---|---|
| 1 | 4 | 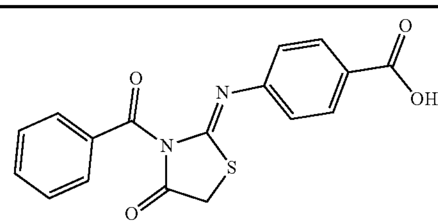 | Scheme 1 (Parent compound) |

-continued
| No of novel compounds | Name according to scheme | structure | Scheme |
|---|---|---|---|
| 2 | 6a | 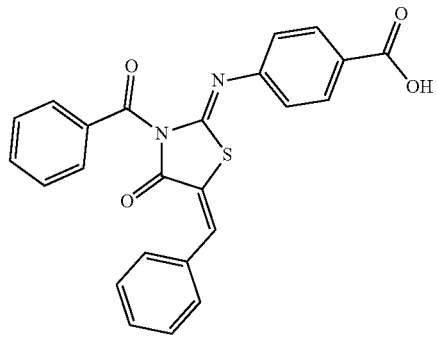 [SMILES: O=C(O)c1ccc(/N=C2\S/C(=C/c3ccccc3)C(=O)N2C(=O)c2ccccc2)cc1] | Scheme 2 |
| 3 | 6b | 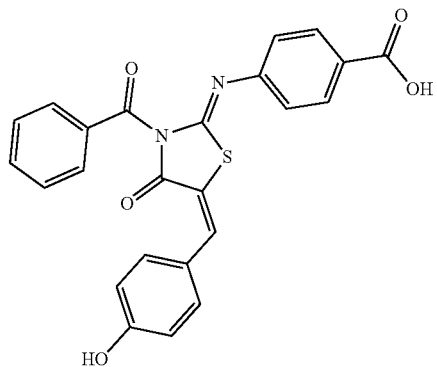 [SMILES: O=C(O)c1ccc(/N=C2\S/C(=C/c3ccc(O)cc3)C(=O)N2C(=O)c2ccccc2)cc1] | Scheme 2 |
| 4 | 6c | 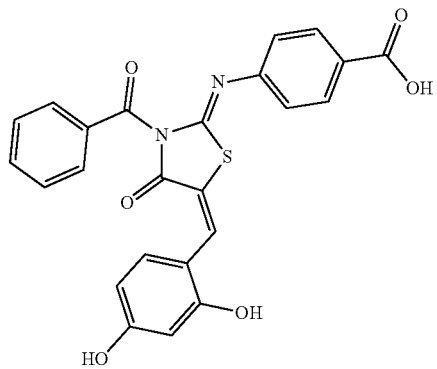 [SMILES: O=C(O)c1ccc(/N=C2\S/C(=C/c3ccc(O)cc3O)C(=O)N2C(=O)c2ccccc2)cc1] | Scheme 2 |
| 5 | 6d | 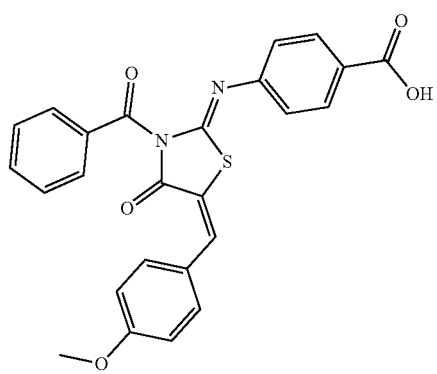 [SMILES: COc1ccc(/C=C2/S/C(=N\c3ccc(C(=O)O)cc3)N(C(=O)c3ccccc3)C2=O)cc1] | Scheme 2 |

-continued
| No of novel compounds | Name according to scheme | structure | Scheme |
|---|---|---|---|
| 6 | 6e | 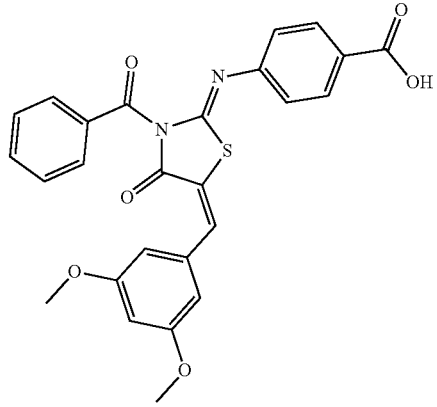 [SMILES: COc1cc(/C=C2/S/C(=N\c3ccc(C(=O)O)cc3)N(C(=O)c3ccccc3)C2=O)cc(OC)c1] | Scheme 2 |
| 7 | 6f | 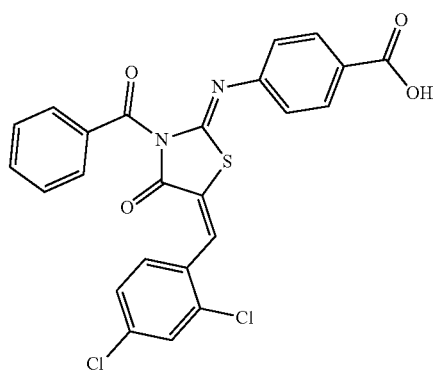 [SMILES: O=C(O)c1ccc(/N=C2\S/C(=C/c3ccc(Cl)cc3Cl)C(=O)N2C(=O)c2ccccc2)cc1] | Scheme 2 |
| 8 | 6g | 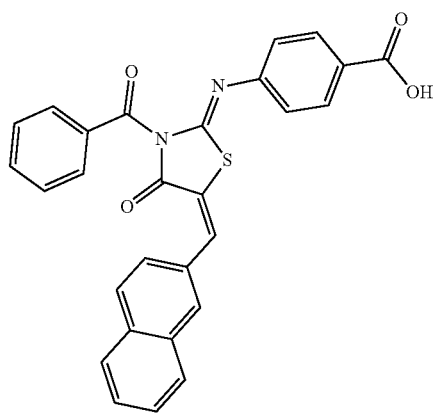 [SMILES: O=C(O)c1ccc(/N=C2\S/C(=C/c3ccc4ccccc4c3)C(=O)N2C(=O)c2ccccc2)cc1] | Scheme 2 |
| 9 | 6h | 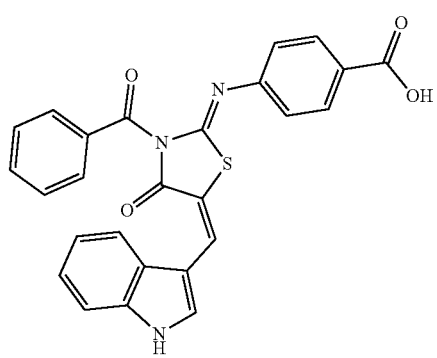 [SMILES: O=C(O)c1ccc(/N=C2\S/C(=C/c3c[nH]c4ccccc34)C(=O)N2C(=O)c2ccccc2)cc1] | Scheme 2 |

-continued
| No of novel compounds | Name according to scheme | structure | Scheme |
|---|---|---|---|
| 10 | 6i | 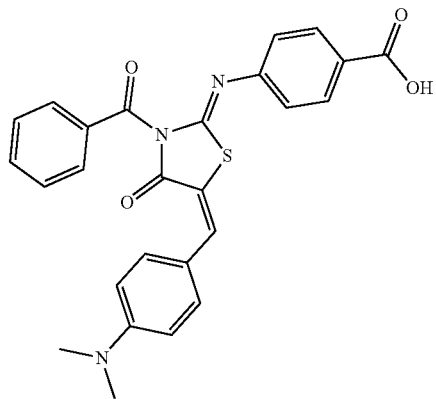 [SMILES: CN(C)c1ccc(/C=C2/S/C(=N\c3ccc(C(=O)O)cc3)N(C(=O)c3ccccc3)C2=O)cc1] | Scheme 2 |
| 11 | 9a | 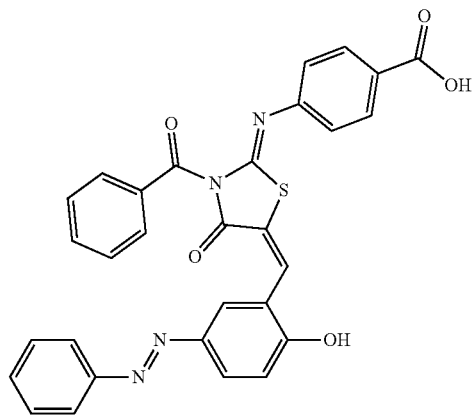 [SMILES: O=C(O)c1ccc(/N=C2\S/C(=C/c3cc(/N=N/c4ccccc4)ccc3O)C(=O)N2C(=O)c2ccccc2)cc1] | Scheme 3 |
| 12 | 9b | 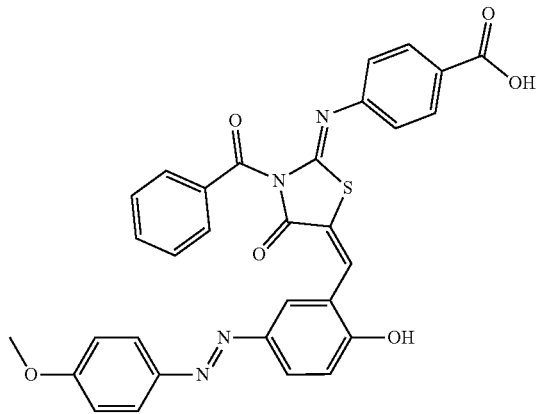 [SMILES: COc1ccc(/N=N/c2ccc(O)c(/C=C3/S/C(=N\c4ccc(C(=O)O)cc4)N(C(=O)c4ccccc4)C3=O)c2)cc1] | Scheme 3 |

-continued

| No of novel compounds | Name according to scheme | structure | Scheme |
|---|---|---|---|
| 13 | 9c | 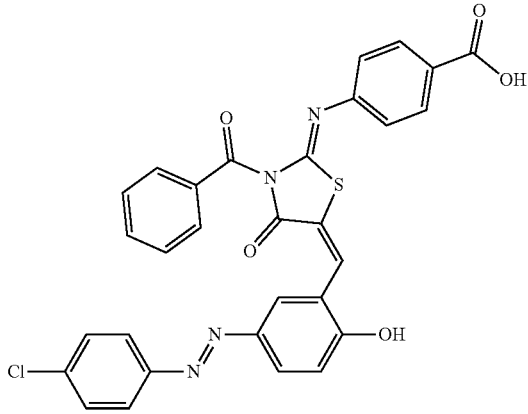 [SMILES: O=C(O)c1ccc(/N=C2\S/C(=C/c3cc(/N=N/c4ccc(Cl)cc4)ccc3O)C(=O)N2C(=O)c2ccccc2)cc1] | Scheme 3 |
| 14 | 10 | 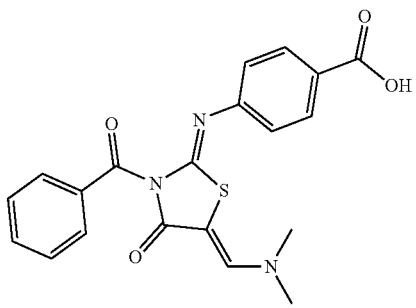 [SMILES: CN(C)/C=C1\S/C(=N\c2ccc(C(=O)O)cc2)N(C(=O)c2ccccc2)C1=O] | Scheme 4 |
| 15 | | 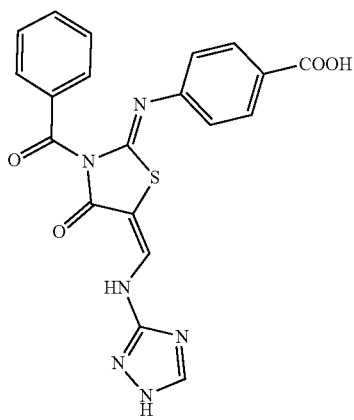 [SMILES: O=C(O)c1ccc(/N=C2\S/C(=C/Nc3nc[nH]n3)C(=O)N2C(=O)c2ccccc2)cc1] | Scheme 4 | and a pharmaceutically acceptable salt, ester, stereoisomer, or solvate thereof.

It is to be understood that the present subject matter covers all combinations of substituent groups referred to herein.

The present compounds may contain, e.g., when isolated in crystalline form, varying amounts of solvents. Accordingly, the present subject matter includes all solvates of the present compounds of formula I and pharmaceutically acceptable stereoisomers, esters, and/or salts thereof. Hydrates are one example of such solvates.

Further, the present subject matter includes all mixtures of possible stereoisomers of the embodied compounds, independent of the ratio, including the racemates.

Salts of the present compounds, or salts of the stereoisomers thereof, include all inorganic and organic acid addition salts and salts with bases, especially all pharmaceutically acceptable inorganic and organic acid addition salts and salts with bases, particularly all pharmaceutically acceptable inorganic and organic acid addition salts and salts with bases customarily used in pharmacy.

Examples of acid addition salts include, but are not limited to, hydrochlorides, hydrobromides, phosphates, nitrates, sulfates, acetates, trifluoroacetates, citrates, D-gluconates, benzoates, 2-(4-hydroxy-benzoyl)benzoates, butyrates, subsalicylates, maleates, laurates, malates, lactates, fumarates, succinates, oxalates, tartrates, stearates, benzenesulfonates (besilates), toluenesulfonates (tosilates), methanesulfonates (mesilates) and 3-hydroxy-2-naphthoates.

Examples of salts with bases include, but are not limited to, lithium, sodium, potassium, calcium, aluminum, magnesium, titanium, ammonium, meglumine and guanidinium salts. The salts include water-insoluble and, particularly, water-soluble salts.

The present compounds, the salts, the stereoisomers and the salts of the stereoisomers thereof may contain, e.g., when isolated in crystalline form, varying amounts of solvents. Included within the present scope are, therefore, all solvates of the compounds of formula I, as well as the solvates of the salts, the stereoisomers and the salts of the stereoisomers of the compounds of formula I.

The present compounds may be isolated and purified in a manner known per se, e.g., by distilling off the solvent in vacuo and recrystallizing the residue obtained from a suitable solvent or subjecting it to one of the customary purification methods, such as column chromatography on a suitable support material.

Salts of the compounds of formula I and the stereoisomers thereof can be obtained by dissolving the free compound in a suitable solvent (by way of non-limiting example, a ketone such as acetone, methylethylketone or methylisobutylketone; an ether such as diethyl ether, tetrahydrofurane or dioxane; a chlorinated hydrocarbon such as methylene chloride or chloroform; a low molecular weight aliphatic alcohol such as methanol, ethanol or isopropanol; a low molecular weight aliphatic ester such as ethyl acetate or isopropyl acetate; or water) which contains the desired acid or base, or to which the desired acid or base is then added. The acid or base can be employed in salt preparation, depending on whether a mono- or polybasic acid or base is concerned and depending on which salt is desired, in an equimolar quantitative ratio or one differing therefrom. The salts are obtained by filtering, reprecipitating, precipitating with a non-solvent for the salt or by evaporating the solvent. Salts obtained can be converted into the free compounds which, in turn, can be converted into salts. In this manner, pharmaceutically unacceptable salts, which can be obtained, for example, as process products in the manufacturing on an industrial scale, can be converted into pharmaceutically acceptable salts by processes known to the person skilled in the art.

Pure diastereomers and pure enantiomers of the present compounds can be obtained, e.g., by asymmetric synthesis, by using chiral starting compounds in synthesis and by splitting up enantiomeric and diastereomeric mixtures obtained in synthesis. Preferably, the pure diastereomeric and pure enantiomeric compounds are obtained by using chiral starting compounds in synthesis.

Enantiomeric and diastereomeric mixtures can be split up into the pure enantiomers and pure diastereomers by methods known to a person skilled in the art. Preferably, diastereomeric mixtures are separated by crystallization, in particular fractional crystallization, or chromatography. Enantiomeric mixtures can be separated, e.g., by forming diastereomers with a chiral auxiliary agent, resolving the diastereomers obtained and removing the chiral auxiliary agent. As chiral auxiliary agents, for example, chiral acids can be used to separate enantiomeric bases and chiral bases can be used to separate enantiomeric acids via formation of diastereomeric salts. Furthermore, diastereomeric derivatives such as diastereomeric esters can be formed from enantiomeric mixtures of alcohols or enantiomeric mixtures of acids, respectively, using chiral acids or chiral alcohols, respectively, as chiral auxiliary agents. Additionally, diastereomeric complexes or diastereomeric clathrates may be used for separating enantiomeric mixtures. Alternatively, enantiomeric mixtures can be split up using chiral separating columns in chromatography. Another suitable method for the isolation of enantiomers is enzymatic separation.

In one embodiment, the present compounds can be prepared according to the following general synthetic pathway. Specifically, synthesis commences with adding benzoyl chloride to potassium isothiocyanate under solvent free conditions. Then microwave irradiation conditions are conducted with a few drops of PEG-400 as solid-liquid phase reaction. The irradiation proceeds for 10 minutes at room temperature with 300-watt power. After the reaction completion, the reactor is cooled to room temperature to obtain compound 2.

Then p-amino benzoic acid (12 mmol) is added slowly with glass rod-shaking for at least about two minutes, or about two minutes. Then the mixture is irradiated at the same conditions for at least about 10 minutes. The mixture is then cooled. After cooling, the formed precipitate is filtered and washed several times with ethanol and water. Finally recrystallization from ethanol gives product 3 as outlined in Scheme 1.

Scheme 1

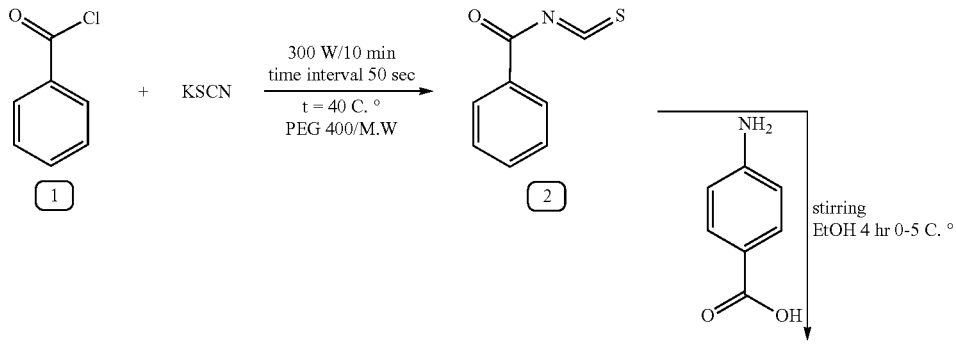

-continued

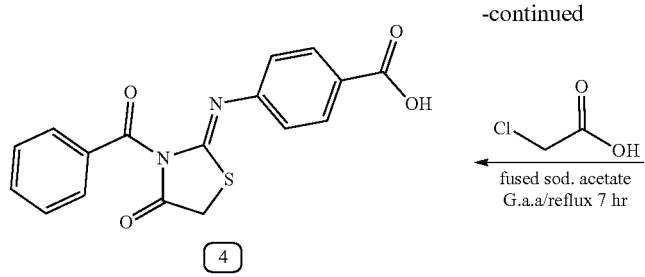

4

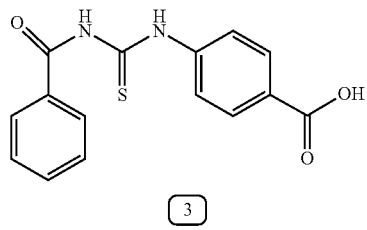

3

Next, a solution of compound 3 in glacial acetic acid is added to an equimolar amount of chloroacetic acid and fused sodium acetate, all of which are placed in a round bottom flask. The reaction proceeds with heating under reflux for at least about 7 hours. After cooling at room temperature, the solid formed is separated by filtration after reducing the To a solution of compound 3 in glacial acetic acid, chloroacetic acid, and fused sodium acetate, an equivalent amount of an appropriate aromatic aldehyde 5a-i is added according to Scheme 2. The mixture is boiled for at least about 4 hours. A yellow cotton like solid is formed. The solid is filtered and washed with hot water and recrystallize from DMF.

Scheme 2

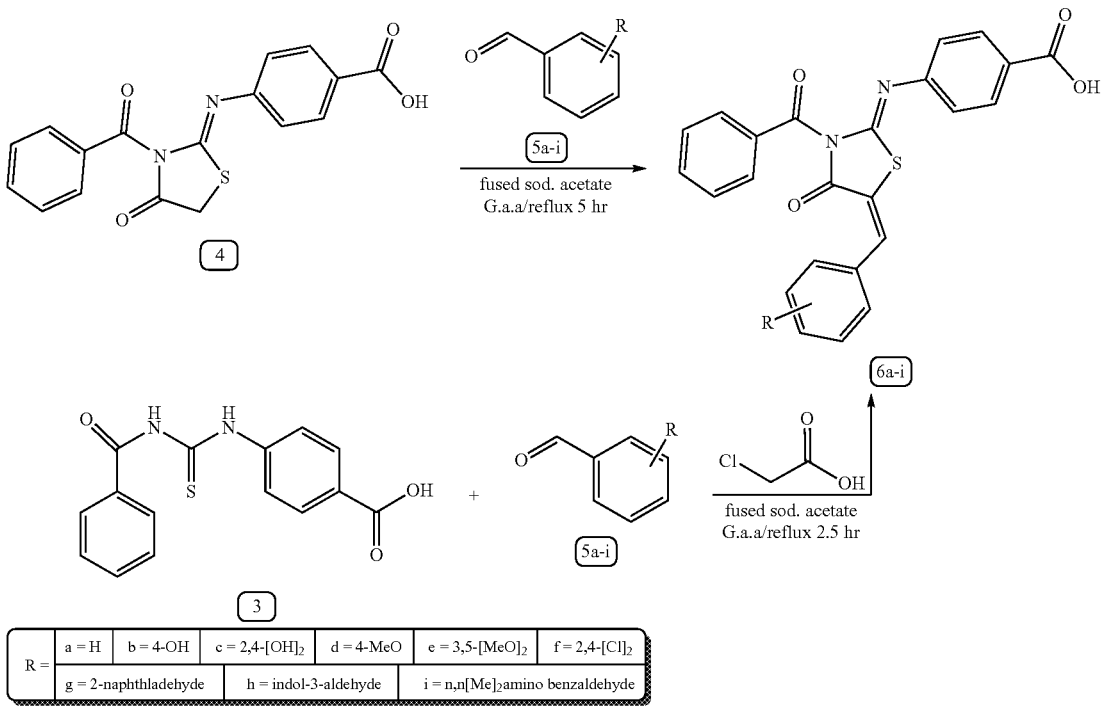

solvent and washed several times with warm water to dispose any excess of chloroacetic acid, then dried and recrystallized from 1,4-dioxane to obtain compound 4 as outlined in Scheme 1.

In an alternate method, compound 4 is obtained using microwave irradiation. A mixture of compound 3 is added to an equimolar amount of chloroacetic acid and fused sodium acetate, all of which are placed in a microwave glass reactor with glacial acetic acid. After the reaction completion, the reactor is allowed to cool to room temperature. The formed precipitate is then filtered and washed several times with hot water. Lastly, compound 4 is recrystallized from 1,4-dioxane.

The procedure to obtain compounds 6a-6i includes three (3) possible methods. The first method is a one pot method.

Alternately, 4-thiazolidinone and appropriate aromatic aldehyde 5a-i are mixed in glacial acetic acid in the presence of equivalent amounts of fused sodium acetate. The mixture is then refluxed for at least about 5 hours, after cooling, the formed solid is separated and worked up as is described above for the one pot method.

A general procedure for preparing compounds 8a-8c, which are intermediates to compounds 9a-9c, includes cooling a mixture of sodium hydroxide and sodium carbonate then stirring the mixture very well until complete dissolution. Then salisaldehyde is added to the mixture and stirred for at least about 10 minutes until the solution becomes yellow. In a small beaker, aniline or any aromatic amine is dissolved in hydrochloric acid and placed in an ice bath for at least about 5 minutes to maintain the temperature between about 0° C. and about 5° C. Then sodium nitrite is dissolved in the solution in the beaker. After shaking, the mixture in the beaker is added dropwise to the solution of salisaldehyde and stirred for one hour at about 0° C. to about 5° C. Then the method includes stirring continued at room temperature for at least about 3 hours. The formed solid is separated by filtration and washed with distilled water several times. The solid is then dried at about 50° C., under vacuum condition, and the solid recrystallized from methanol as outlined in Scheme 3.

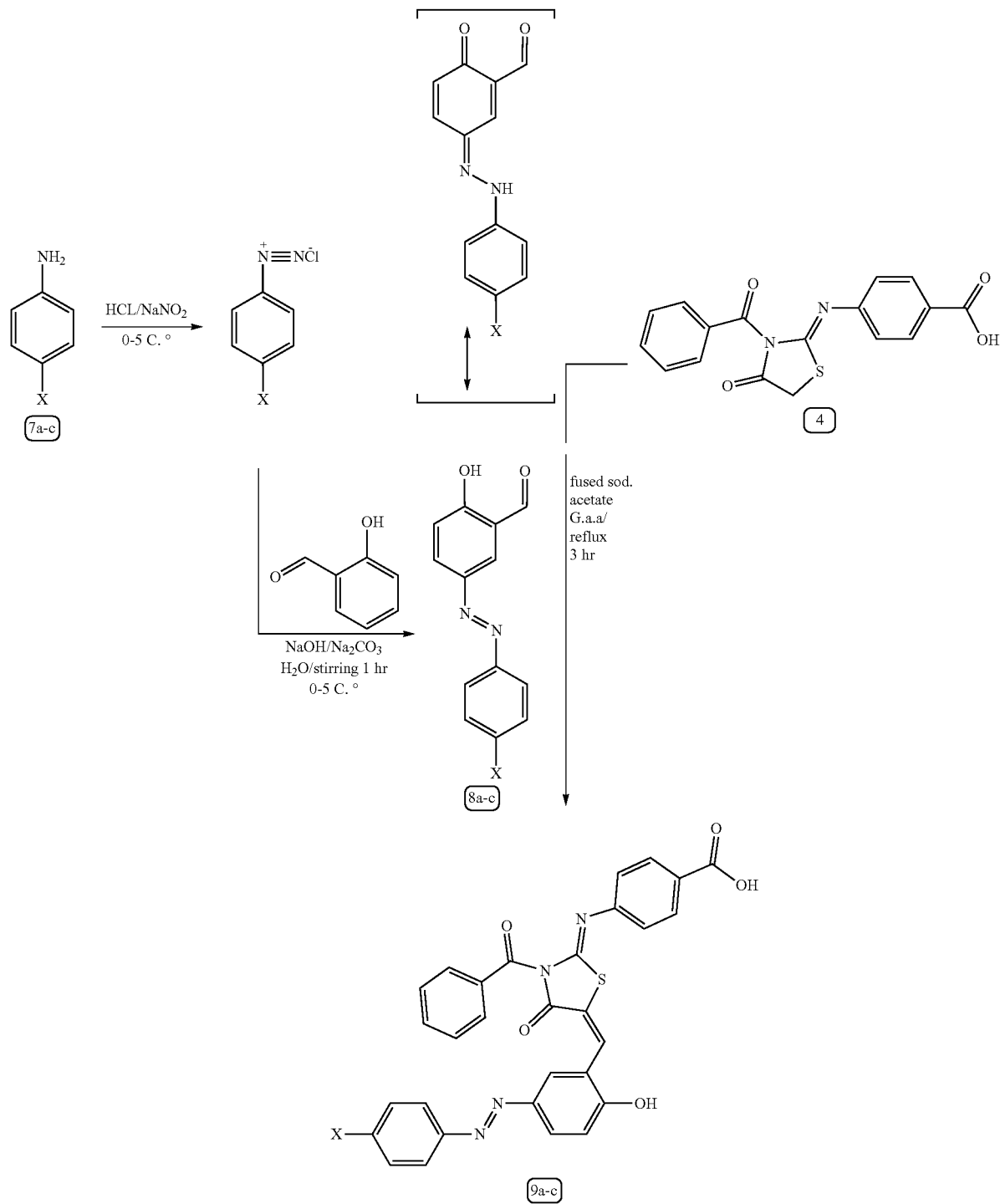

The process to obtain compounds 9a-9c continues with mixing 4-thiazolidinone and an appropriate azo salicylaldehyde derivatives 8a-c together in glacial acetic acid in the presence of equivalent amounts of fused sodium acetate. The mixture is refluxed for at least about 3 hours. After cooling, the formed solid is separated by filtration and washed with distilled water. The solid is then dried at about 50° C. and the solid is recrystallized as outlined in Scheme 3.

The procedure to prepare compound 10 includes mixing 4-thiazolidinone and dimethylformamide dimethylacetal (DMF-DMA) together. The mixture is then heated under reflux for at least 3 hours without a solvent. The mixture is cooled and then the formed solid is separated, filtered, and washed with commercial ethanol and recrystallized from 1,4-dioxane as outlined in Scheme 4.

In another embodiment, the present pharmaceutical compositions may further include an encapsulation of one or more of the present compounds comprising a nanostructure lipid carrier and a chitosan core shell.

Non-limiting examples of suitable excipients, carriers, or vehicles useful herein include liquids such as water, saline, glycerol, polyethylene glycol, hyaluronic acid, ethanol, and the like. Suitable excipients for nonliquid formulations are also known to those of skill in the art. A thorough discussion of pharmaceutically acceptable excipients and salts useful herein is available in Remington's Pharmaceutical Sciences, 18th Edition. Easton, Pa., Mack Publishing Company, 1990, the entire contents of which are incorporated by reference herein.

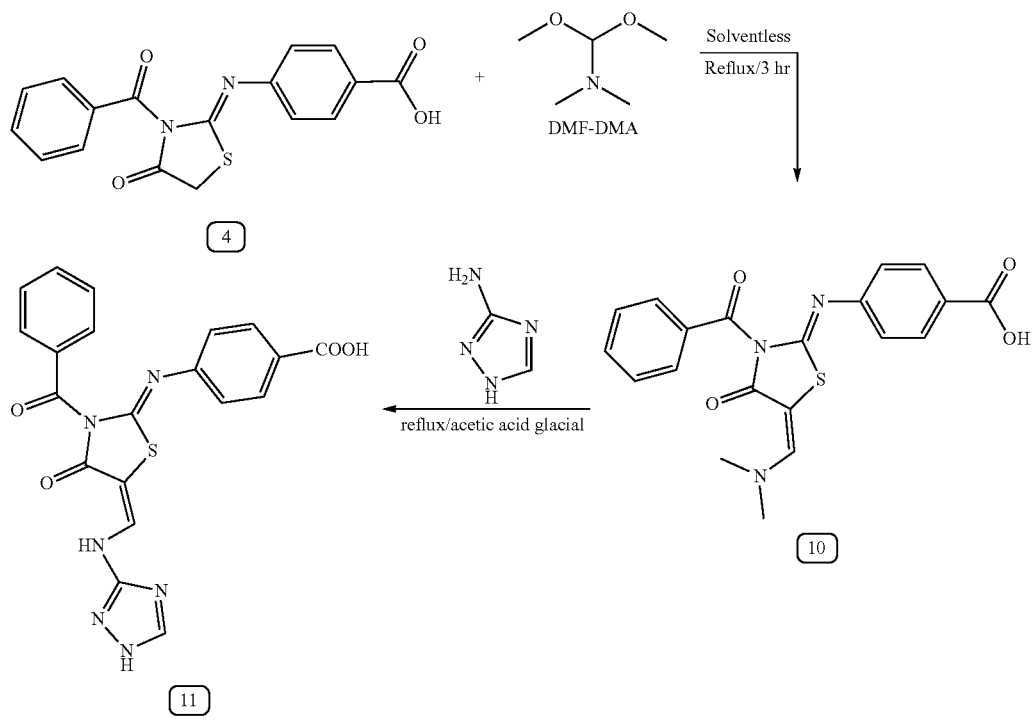

An additional compound 11 can then be synthesized by mixing enaminone 10 and 1H-1,2,4-triazol-3-amine together in glacial acetic acid. The mixture is refluxed for at least about 5 hours and then cooled. After cooling, the formed solid is separated and washed with commercial ethanol and recrystallized from DMFIn another embodiment, the present subject matter is directed to pharmaceutical compositions comprising a therapeutically effective amount of the compounds as described herein together with one or more pharmaceutically acceptable carriers, excipients, or vehicles. In some embodiments, the present compositions can be used for combination therapy, where other therapeutic and/or prophylactic ingredients can be included therein.

The present subject matter further relates to a pharmaceutical composition, which comprises at least one of the present compounds together with at least one pharmaceutically acceptable auxiliary.

In an embodiment, the pharmaceutical composition comprises one or two of the present compounds, or one of the present compounds.

The present compounds are typically administered at a therapeutically or pharmaceutically effective dosage, e.g., a dosage sufficient to provide treatment for cancer. Administration of the compounds or pharmaceutical compositions thereof can be by any method that delivers the compounds systemically and/or locally. These methods include oral routes, parenteral routes, intraduodenal routes, and the like.

While human dosage levels have yet to be optimized for the present compounds, generally, a daily dose is from about 0.01 to 10.0 mg/kg of body weight, for example about 0.1 to 5.0 mg/kg of body weight. The precise effective amount will vary from subject to subject and will depend upon the species, age, the subject's size and health, the nature and extent of the condition being treated, recommendations of the treating physician, and the therapeutics or combination of therapeutics selected for administration. The subject may be administered as many doses as is required to reduce and/or alleviate the signs, symptoms, or causes of the disease or disorder in question, or bring about any other desired alteration of a biological system.

In employing the present compounds for treatment of cancer, any pharmaceutically acceptable mode of administration can be used with other pharmaceutically acceptable excipients, including solid, semi-solid, liquid or aerosol dosage forms, such as, for example, tablets, capsules, powders, liquids, suspensions, suppositories, aerosols or the like. The present compounds can also be administered in sustained or controlled release dosage forms, including depot injections, osmotic pumps, pills, transdermal (including electrotransport) patches, and the like, for the prolonged administration of the compound at a predetermined rate, preferably in unit dosage forms suitable for single administration of precise dosages.

The present compounds may also be administered as compositions prepared as foods for humans or animals, including medical foods, functional food, special nutrition foods and dietary supplements. A "medical food" is a product prescribed by a physician that is intended for the specific dietary management of a disorder or health condition for which distinctive nutritional requirements exist and may include formulations fed through a feeding tube (referred to as enteral administration or gavage administration).

A "dietary supplement" shall mean a product that is intended to supplement the human diet and may be provided in the form of a pill, capsule, tablet, or like formulation. By way of non-limiting example, a dietary supplement may include one or more of the following dietary ingredients: vitamins, minerals, herbs, botanicals, amino acids, and dietary substances intended to supplement the diet by increasing total dietary intake, or a concentrate, metabolite, constituent, extract, or combinations of these ingredients, not intended as a conventional food or as the sole item of a meal or diet. Dietary supplements may also be incorporated into foodstuffs, such as functional foods designed to promote control of glucose levels. A "functional food" is an ordinary food that has one or more components or ingredients incorporated into it to give a specific medical or physiological benefit, other than a purely nutritional effect. "Special nutrition food" means ingredients designed for a particular diet related to conditions or to support treatment of nutritional deficiencies.

Generally, depending on the intended mode of administration, the pharmaceutically acceptable composition will contain about 0.1% to 90%, for example about 0.5% to 50%, by weight of a compound or salt of the present compounds, the remainder being suitable pharmaceutical excipients, carriers, etc.

One manner of administration for the conditions detailed above is oral, using a convenient daily dosage regimen which can be adjusted according to the degree of affliction. For such oral administration, a pharmaceutically acceptable, non-toxic composition is formed by the incorporation of any of the normally employed excipients, such as, for example, mannitol, lactose, starch, magnesium stearate, sodium saccharine, talcum, cellulose, sodium croscanmellose, glucose, gelatin, sucrose, magnesium carbonate, and the like. Such compositions take the form of solutions, suspensions, tablets, dispersible tablets, pills, capsules, powders, sustained release formulations and the like.

The present compositions may take the form of a pill or tablet and thus the composition may contain, along with the active ingredient, a diluent such as lactose, sucrose, dicalcium phosphate, or the like; a lubricant such as magnesium stearate or the like; and a binder such as starch, gum acacia, polyvinyl pyrrolidine, gelatin, cellulose, and derivatives thereof, and the like.

Liquid pharmaceutically administrable compositions can, for example, be prepared by dissolving, dispersing, etc. an active compound as defined above and optional pharmaceutical adjuvants in a carrier, such as, for example, water, saline, aqueous dextrose, glycerol, glycols, ethanol, and the like, to thereby form a solution or suspension. If desired, the pharmaceutical composition to be administered may also contain minor amounts of nontoxic auxiliary substances such as wetting agents, emulsifying agents, or solubilizing agents, pH buffering agents and the like, for example, sodium acetate, sodium citrate, cyclodextrin derivatives, sorbitan monolaurate, triethanolamine acetate, triethanolamine oleate, etc.

For oral administration, a pharmaceutically acceptable non-toxic composition may be formed by the incorporation of any normally employed excipients, such as, for example, pharmaceutical grades of mannitol, lactose, starch, magnesium stearate, talcum, cellulose derivatives, sodium croscarmellose, glucose, sucrose, magnesium carbonate, sodium saccharin, talcum and the like. Such compositions take the form of solutions, suspensions, tablets, capsules, powders, sustained release formulations and the like.

For a solid dosage form, a solution or suspension in, for example, propylene carbonate, vegetable oils or triglycerides, may be encapsulated in a gelatin capsule. Such diester solutions, and the preparation and encapsulation thereof, are disclosed in U.S. Pat. Nos. 4,328,245; 4,409,239; and 4,410,545, the contents of each of which are incorporated herein by reference. For a liquid dosage form, the solution, e.g., in a polyethylene glycol, may be diluted with a sufficient quantity of a pharmaceutically acceptable liquid carrier, e.g., water, to be easily measured for administration.

Alternatively, liquid or semi-solid oral formulations may be prepared by dissolving or dispersing the active compound or salt in vegetable oils, glycols, triglycerides, propylene glycol esters (e.g., propylene carbonate) and the like, and encapsulating these solutions or suspensions in hard or soft gelatin capsule shells.

Other useful formulations include those set forth in U.S. Pat. Nos. Re. 28,819 and 4,358,603, the contents of each of which are hereby incorporated by reference.

Another manner of administration is parenteral administration, generally characterized by injection, either subcutaneously, intramuscularly, or intravenously. Injectables can be prepared in conventional forms, either as liquid solutions or suspensions, solid forms suitable for solution or suspension in liquid prior to injection, or as emulsions. Suitable excipients are, for example, water, saline, dextrose, glycerol, ethanol or the like. In addition, if desired, the pharmaceutical compositions to be administered may also contain minor amounts of non-toxic auxiliary substances such as wetting or emulsifying agents, pH buffering agents, solubility enhancers, and the like, such as for example, sodium acetate, sorbitan monolaurate, triethanolamine oleate, cyclodextrins, etc.

Another approach for parenteral administration employs the implantation of a slow-release or sustained-release system, such that a constant level of dosage is maintained. The percentage of active compound contained in such parenteral compositions is highly dependent on the specific nature thereof, as well as the activity of the compound and the needs of the subject. However, percentages of active ingredient of 0.01% to 10% in solution are employable and will be higher if the composition is a solid which will be subsequently diluted to the above percentages. The composition may comprise 0.2% to 2% of the active agent in solution.

Nasal solutions of the active compound alone or in combination with other pharmaceutically acceptable excipients can also be administered.

Formulations of the active compound or a salt may also be administered to the respiratory tract as an aerosol or solution for a nebulizer, or as a microfine powder for insufflation, alone or in combination with an inert carrier such as lactose. In such a case, the particles of the formulation have diameters of less than 50 microns, for example less than 10 microns.

The present compounds have valuable pharmaceutical properties, which make them commercially utilizable. Accordingly, the present subject matter further relates to use of the present compounds for the treatment of diseases such as cancers. Similarly, the present compounds can be used to inhibit epidermal growth factor receptor (EGFR) activity in a patient.

In another embodiment of the present subject matter, the aforementioned compound derivatives demonstrated anticancer action against human cancer cell lines such as MCF7 (breast cancer), PC3 (prostate cancer), and HCT 116 (colon cancer). Accordingly, the present subject matter relates to methods of treating a cancer in a patient by administering one or more of the compounds presented herein to a patient in need thereof. In certain embodiments, the cancer treatable with the present compounds is one or more selected from the group consisting of colon cancer, prostate cancer, and breast cancer.

Accordingly, in an embodiment of the present subject matter, the heterocyclic 4-thiazolidinone compounds as described herein engaged for in vitro study towards human cancer cell lines can display an $IC_{50}$ with a nano to micromolar concentration range. For example, certain of the present compounds engaged for in vitro study against PC3 (prostate) cancer cell lines can display $IC_{50}$ values ranging from 67.39 µM to 98.49 µM.

In another embodiment, certain of the present compounds engaged for in vitro study against HCT 116 (colon) cancer cell lines can display $IC_{50}$ values ranging from 7.17 µM to 19.57 µM.

In one embodiment, certain of the present compounds engaged for in vitro study against MCF7 (breast) cancer cell lines can display $IC_{50}$ values ranging from 11.74 µM to 38.04 µM.

The most activated drugs' enzyme inhibition and cell cycle apoptosis can be determined further after encapsulation in a nanostructure lipid carrier and chitosan core shell and re-assessed according to anticancer and enzyme inhibition assays. Compound 6c's enzyme assay in addition to antitumor activities were enhanced and $IC_{50}$ was reduced by twice of its original data before encapsulation. The apoptotic and necrotic properties were promising. Compound 6c's nanoformulation strongly makes cell arrest at cell growth arrest at G2/M stage.

The present subject matter further relates to a method of treating or preventing a disease comprising administering to a patient in need thereof a therapeutically effective amount of at least one of the compounds herein.

In particular, the present subject matter relates to a method of treating one of the above-mentioned diseases or disorders comprising administering to a patient in need thereof a therapeutically effective amount of at least one of the compounds herein.

In the above methods, the patient is preferably a mammal, more preferably a human. Furthermore, in the above methods, at least one of the present compounds can be used. In an embodiment, one or two of the present compounds are used, or one of the present compounds is used. Similarly, one or more of the present compounds can be used in combination therapy with one or more additional active agents.

The following examples relate to various methods of manufacturing certain specific compounds as described herein. All compound numbers expressed herein are with reference to the synthetic pathway figures shown above.

EXAMPLES

Example 1

Preparation of General Procedure for the Synthesis of 4-(3-Benzoylthioureido)Benzoic Acid (3

With little modification a mixture of benzoyl chloride (12 mmol) and potassium isothiocyanate (12 mmol) under solvent free and microwave irradiation conditions with few drops of PEG-400 as solid-liquid phase reaction, the irradiation proceeded for 10 minutes at room temperature with 300-watt power and 0.5 sec time interval. After the reaction completed, the reactor was cooled at room temperature to obtain compound 2 as illustrated in Scheme 1 above. The completed without working up through the addition of p-amino benzoic acid (12 mmol) was added slowly with glass rod-shaking for two minutes, then the mixture irradiated at the same condition for 10 minutes, after cooling, the formed precipitate was filtered and washed several times with 75% ethanol and water, finally recrystallize from ethanol to give product 3.

White crystals; yield 68.8% thermal (95% microwave); m.p=177-179° C.; IR (KBr, cm$^{-1}$): 3174 (NH), 3108 (NH), 1265 (C=S); $^1$H NMR (DMSO-d$_6$): δ=7.54 (t, 2H, J=6.16 Hz, Ar), 7.60 (t, 1H, J=5.84 Hz, Ar), δ=7.66 (t, 2H, J=5.96 Hz, Ar), 7.94-8.04 (m, 4H, Ar), 10.60 (s, 1H, NH, exchangeable D$_2$O), 11.68 (s, 1H, NH, exchangeable D$_2$O), 12.87 (s, 1H, OH, exchangeable D$_2$O); MS: m/z (%)=323 (M$^+$+1, 12.5), 299 (M$^+$, 43.5), Anal. Calcd for $C_{15}H_{12}N_2O_3S$ (300.06): C59.78; H, 3.80; N, 15.88; S, 10.59C. Found: 59.99; H, 4.03; N, 9.33; O, S, 10.67%.

Example 2

Preparation of for the Synthesis of (4-((3-Benzoyl-4-Oxothiazolidin-2-Ylidene)Amino)Benzoic Acid (4

Method 1 (Conventional Thermal):

A solution of compound 3 (0.05 M) in 20 ml glacial acetic acid was added to an equi-molar amount of chloroacetic acid (0.05 M) and fused sodium acetate (0.05 M) of were placed in round bottom flask, the reaction proceed to heat under reflux for 7 hr. after cooling at room temperature the solid formed separated by filtration after reducing the solvent and washed several times with worm water to dispose any excess of fused sodium acetate then dried and recrystallized from 1,4-dioxane.

Method II (Microwave Irradiation):

A mixture of compound 3 (5 mmol) was added to an equimolar amount of chloroacetic acid (5 mmol) and fused sodium acetate (5 mmol) of were placed in Microwave glass reactor with 1 ml glacial acetic acid and entry sets were, temperature 25° C., 300 watt for 30 minutes with 0.5 sec time intervals after the reaction completion. The reactor was left to cool at room temperature. Then the formed precipitate was filtered and washed several times with hot water, and finally recrystallized from 1,4-dioxane.

Yellow crystals; yield 87%; m.p=230-232° C. IR (KBr, cm$^{-1}$): 1728(C=O, Thiazole ring); 1743(C=O, carboxylic group); 1H NMR (DMSO-d$_6$): δ=4.18 (s, 2H, CH$_2$), 7.94 (d, 2H, J=8.7 Hz, Ar), 8.13 (d, 2H, J=8.4 Hz, Ar), 7.43-7.89 (m, 5H, Ar), 12.77 (s, 1H, COOH, exchangeable D$_2$O); $^{13}$C NMR (DMSO-d$_6$): δ=21.41, 44.8, 69.6, 119.6, 120.02, 122.6, 128.3, 131.6, 132.8, 134.6, 139.05, 165.73, 172.50, 178.6. MS: MS: m/z (%)=340 (M$^+$, 2.5), 298 (2.03), 263 (1.46), 205 (6.19), 105 (100), 77 (48.9), Anal. Calcd. for C$_{17}$H$_{12}$N$_2$O$_4$S (340.35): C59.99; H, 3.55; N, 8.23; S, 9.42. Found: C59.79; H, 3.34; N, 8.06; S, 9.19%

Example 3

General Procedure for the Synthesis of 6a-i

Method I (One Pot):
To a solution of compound 3 (5 mmol) in 15 mL glacial acetic acid, chloroacetic acid (5 mmol) and fused sodium acetate (5 mmol), an equivalent amount of appropriate aromatic aldehyde 5a-i. The mixture was boiled for 4 hours, yellow cotton like solid was formed, solid filtered and washed with hot water three times and recrystallize from DMF.

Method II (Thermal):
4-Thiazolidinone (5 mmol) and appropriate aromatic aldehyde 5a-i (5 mmol) are mixed in 20 mL of glacial acetic acid in the presence of equivalent amounts of fused sodium acetate. The mixture refluxed for 5 hours, after cooling, the formed solid separated and worked up as the one pot method.

Method III (Microwave Irradiation):
A mixture of thiazolidinone 4 (5 mmol) and appropriate aromatic aldehyde 5a-i (5 mmol) were placed in a microwave glass reactor with 1 mL PEG 400 and a of temperature 25° C., 300 watt for 12 min with 0.5 second time interval after the reaction completion. The reactor was allowed to cool to room temperature. Then the formed precipitate was filtered and washed several time with commercial ethanol. Finally, the compounds were recrystallizes from DMF.

Example 4

Characterization of 4-(3-Benzoyl-5-Benzylidene-4-Oxothiazolidin-2-Ylidene)Amino)Benzoic Acid (6a Yellow crystals; yield 71.6% (thermal), 86.6% (one pot), 98.01% (microwave); m.p=248-260° C.; IR (KBr, cm$^{-1}$): 1726(C=O, Thiazole ring); 1738(C=O, carboxylic group); $^1$H NMR (DMSO-d$_6$): δ=7.42-7.93 (m, 12H, Ar), 8.17 (d, 2H, J=8.4 Hz, Ar), 8.25 (d, 2H, J=8.4 Hz, Ar), 12.55 (s, 1H, COOH, exchangeable D$_2$O) MS: MS: m/z (%)=428 (M$^+$, 25.6), 263 (6.46), 205 (12.42), 105 (60.5), 77 (44.2), Anal. Calcd. for C$_{24}$H$_{16}$N$_2$O$_4$S (428.46): C, C67.28; H, 3.76; N, 6.54; S, 7.48. Found: 67.09; H, 3.58; N, 6.32; S, 7.32%

Example 5

Characterization of 4-(3-Benzoyl-5-(4-Hydroxybenzylidene)-4-Oxothiazolidin-2-Ylidene)Amino)Benzoic Acid (6b Yellow crystals; yield 79.5% (thermal), 84.9% (one pot), 97.8% (microwave); m.p=264-266° C.; IR (KBr, cm$^{-1}$): 1722(C=O, Thiazole ring); 1731(C=O, carboxylic group); $^1$H NMR (DMSO-d$_6$): δ=6.93 (d, 2H, J=8.5 Hz, Ar), 7.45-7.97 (m, 10H, Ar), 8.14 (d, 2H, J=8.4 Hz, Ar), 10.27 (s, 1H, OH, exchangeable D$_2$O); 10.54 (s, 1H, COOH, exchangeable D$_2$O) MS: MS: m/z (%)=444 (M$^+$, 10.5), 263 (3.46), 205 (9.22), 105 (100), 77 (36.6), Anal. Calcd. for C$_{24}$H$_{16}$N$_2$O$_5$S (444.46): C64.86; H, 3.63; N, 6.30; S, 7.21. Found: C64.73; H, 3.53; N, 6.10; S, 7.04%.

Example 6

Characterization of 4-(3-Benzoyl-5-(2,4-Dihydroxybenzylidene)-4-Oxothiazolidin-2-Ylidene)Amino) Benzoic Acid (6c Pale Yellow crystals; yield 52.2% (thermal), 57.4% (one pot), 71.2% (microwave); m.p=266-268° C.; IR (KBr, cm$^{-1}$): 1721 (C=O, Thiazole ring); 1732(C=O, carboxylic group); $^1$H NMR (DMSO-d$_6$): δ=6.95 (d, 2H, J=8.4 Hz, Ar), 7.45-7.97 (m, 9H, Ar), 8.18 (d, 2H, J=8.2 Hz, Ar), 10.46 (s, 1H, OH, exchangeable D$_2$O), 10.92 (s, 1H, OH, exchangeable D$_2$O); 10.32 (s, 1H, COOH, exchangeable D$_2$O); MS: MS: m/z (%)=460 (M$^+$, 10.3), 192 (14.42), 105 (55.5), 77 (14.1), Anal. Calcd. for C$_{24}$H$_{16}$N$_2$O$_6$S (460.46): C62.39; H, 3.36; N, 6.08; S, 6.86 Found: 62.60; H, 3.50; N, 6.08; S, 6.96%

Example 7

Characterization of 4-(3-Benzoyl-5-(4-Methoxybenzylidene)-4-Oxothiazolidin-2-Ylidene)Amino)Benzoic Acid (6d Bright Yellow crystals; yield 88.5% (thermal), 89.9% (one pot), 94.9% (microwave); m.p=274-276° C.; IR (KBr, cm$^{-1}$): 1717 (C=O, Thiazole ring); 1728(C=O, carboxylic group); $^1$H NMR (DMSO-d$_6$): δ=3.26 (s, 3H, CH$_3$), 6.91 (d, 2H, 1=7.9 Hz, Ar), 7.32-7.45 (m, 7H, Ar), 7.49 (s, 1H, CH, Ar), 7.81 (d, 2H, J=8.2 Hz, Ar), 8.11 (d, 2H, J=8.4 Hz, Ar), 10.48 (s, 1H, COOH, exchangeable D$_2$O); MS: MS: m/z (%)=458 (M$^+$, 72.9), 105 (66.7), 77 (26.6), Anal. Calcd. for C$_{25}$H$_{18}$N$_2$O$_5$S (458.49): C65.39; H, 4.06; N, 6.32; S, 7.15. Found: C65.49; H, 3.96; N, 6.11; S, 6.99%.

Example 8

Characterization of 4-(3-Benzoyl-5-(3.5-Dihydroxybenzylidene)-4-Oxothiazolidin-2-Ylidene)Amino) Benzoic Acid (6e Bright Yellow crystals; yield 89.8% (thermal), 88.3% (one pot), 98.8% (microwave); m.p=272-274° C.; IR (KBr, cm$^{-1}$): 1714 (C=O, Thiazole ring); 1722(C=O, carboxylic group); $^1$H NMR (DMSO-d$_6$): δ=3.21 (s, 6H, CH$_3$), 6.45 (s, 1H, Ar), 6.69 (d, 2H, J=8.4 Hz, Ar), 7.31-7.44 (m, 5H, Ar), 7.48 (s, 1H, CH, Ar), 7.80 (d, 2H, J=8.2 Hz, Ar), 8.09 (d, 2H, J=8.4 Hz, Ar), 10.47 (s, 1H, COOH, exchangeable D$_2$O); MS: MS: m/z (%)=488.51 (M$^+$, 19.61), 194 (50.97) 105 (100.0), 77 (60.64), Anal. Calcd. for C$_{26}$H$_{20}$N$_2$O$_6$S (488.51): C63.66; H, 4.00; N, 5.92; S, 6.49. Found: C63.93; H, 4.13; N, 5.73; S, 6.56%.

Example 9

Characterization of 4-(3-Benzoyl-5-(2.4-Dichlorobenzylidene)-4-Oxothiazolidin-2-Ylidene)Amino) Benzoic Acid (6f Pale Yellow crystals; yield 40.8% (thermal), 59.1% (one pot), 88.8% (microwave); m.p=280-282° C.; IR (KBr, cm$^{-1}$): 1712 (C=O, Thiazole ring); 1721(C=O, carboxylic group); $^1$H NMR (DMSO-d$_6$): δ=7.39-7.52 (m, 10H, Ar), 7.55 (s, 1H, CH, Ar), 8.04 (d, 2H, J=8.4 Hz, Ar), 10.80 (s, 1H, COOH, exchangeable D$_2$O); Anal. Calcd. for C$_{24}$H$_{14}$Cl$_2$N$_2$O$_4$S (497.35): C57.80; H, 2.62; N, 5.68; S, 6.52. Found: C57.96; H, 2.84; N, 5.63; S, 6.45%.

Example 10

Characterization of 4-(3-Benzoyl-5-(Naphthalen-2-Ylmethylene)-4-Oxothiazolidin-2-Ylidene)Amino)-Benzoic Acid (6g Pale Yellow crystals; yield 60.1% (thermal), 65.3% (one pot), 79.5% (microwave); m.p=278-280° C.; IR (KBr, cm$^{-1}$): 1714 (C=O, Thiazole ring); 1728(C=O, carboxylic group); $^1$H NMR (DMSO-d$_6$): δ=7.39 (d, 2H, J=7.6 Hz, Ar), 7.45-7.89 (m, 13H, Ar), 8.10 (d, 2H, J=8.4 Hz, Ar), 10.80 (s, 1H, COOH, exchangeable D$_2$O); MS: MS: m/z (%)=478 (M$^+$, 49.55), 194 (33.97) 105 (89.08), 77 (59.56), Anal. Calcd. for C$_{28}$H$_{18}$N$_2$O$_4$S (478.52): C70.11; H, 3.69; N, 5.71; S, 6.49. Found: C70.28; H, 3.79; N, 5.85; S, 6.70%.

Example 11

Characterization of 4-(5-((1H-Indol-3-Yl)Methylene)-3-Benzoyl-4-Oxothiazolidin-2-Ylidene)Amino) Benzoic Acid (6h Yellow crystals; yield 66.16% (thermal), 76.5% (one pot), 88.4% (microwave); m.p=258-260° C.; IR (KBr, cm$^{-1}$): 3429 (NH), 1729 (C=O, Thiazole ring); 1736(C=O, carboxylic group); $^1$H NMR (DMSO-d$_6$): δ=7.29-7.67 (m, 9H, Ar), 7.72 (s, 1H, CH, Ar), 7.76 (s, 1H, CH, Ar), 7.97 (d, 2H, CH, Ar), 8.25 (d, 2H, J=8.4 Hz, Ar), 11.22 (s, 1H, COOH, exchangeable D$_2$O), 12.10 (s, 1H, NH, exchangeable D$_2$O); MS: MS: m/z (%)=478 (M$^+$, 22.10), 194 (50.29) 105 (80.12), 77 (38.15), Anal. Calcd. for C$_{26}$H$_7$N$_3$O$_4$S (467.50): C66.60; H, 3.57; N, 9.15; S, 6.70. Found: C66.80; H, 3.67; N, 8.99; S, 6.86%.

Example 12

Characterization of 4(3-Benzoyl-5-(4-(Dimethylamino)Benzylidene)-4-Oxothiazolidin-2-Ylidene) Amino)Benzoic Acid (6i Orange crystals; yield 71.5% (thermal), 77.9% (one pot), 95.2% (microwave) m.p=282-284° C.; IR (KBr, cm$^{-1}$): 1712(C=O, Thiazole ring); 1723 (C=O, carboxylic group); $^1$H NMR (DMSO-d$_6$): δ=3.12 (s, 6H, CH$_3$), 6.88 (d, 2H, J=7.2 Hz, Ar), 7.47-7.67 (m, 7H, Ar), 7.77 (s, 1H, Ar), 7.98 (d, 2H, J=7.8 Hz, Ar), 8.15 (d, 2H, 1=8.4 Hz, Ar), 11.33 (s, 1H, COOH, exchangeable D$_2$O); MS: MS: m/z (%)=471.53 (M$^+$, 32.4), 194 (50.29), 105 (52.3), 77 (42.3), Anal. Calcd. for C$_{26}$H$_{21}$N$_3$O$_4$S (471.53): C, 66.00; H, 4.29; N, 8.70; S, 6.99. Found: C66.23; H, 4.49; N, 8.91; S, 6.80.% (n,n di methyl amino)

Example 13

General Preparation of Compounds 8a-8c

In a 250 mL beaker containing 150 mL of ice cooled distilled water, a mixture of 1.6 g, 40 mmol sodium hydroxide and 29.2 g, 275 mmol of sodium carbonate was stirred very well until complete dissolution. This was followed by addition of 4.2 mL, 34 mmol salisaldehyde and stirred for 10 minutes. Then the solution became yellow. In a small beaker, 3.68 mL, 39 mmol of aniline or any aromatic amine was dissolved in 12 mL of concentrated hydrochloric acid and placed in ice bath for 5 minutes to keep its temperature between 0-5° C. Then 2.76g, 40 mmol of sodium nitrite was dissolved in the least amount of distilled water. After shaking very well, the solution in the small beaker was added dropwise to the beaker containing the solution of salisaldehyde in the 250 mL beaker. The solution was stirred for one hour at 0-5° C. Stirring then continued at room temperature for 3 hours. The solid formed was separated by filtration and washed 5 times with distilled water. Then the solid was dried at 50° C. and the solid was recrystallized from methanol.

Example 14

Characterization of 2-Hydroxy-5-(Phenyldiazenyl)Benzaldehyde (8a

Red powder; yield 69.5%; m.p=110-112° C.; IR (KBr, cm$^{-1}$): 1680(C=O); $^1$H NMR (DMSO-d$_6$): δ=7.13-8.29 (m, 8H, Ar), 9.14 (s, 1H, OH, exchangeable D$_2$O) 10.37 (s, 1H, CHO, exchangeable D$_2$O); MS: MS: m/z (%)=: 226 (M$^+$, 9.4); Anal. Calcd. for C$_3$H$_{10}$N$_2$O$_2$ (226.24): C68.79; H, 4.46; N, 12.38. Found: C69.02; H, 4.46; N, 12.38%.

Example 17

General Procedure for the Synthesis of 9a-c 4-thiazolidinone and an appropriate azo salisaldehyde derivative 8a-c, of Example 13, (5 mmol) were mixed in 20 mL of glacial acetic acid in the presence of equivalent amounts of fused sodium acetate. The mixture was refluxed for 3 hours. After cooling, the formed solid separated by filtration and recrystallized.

Example 18

Characterization of 4-(-3-Benzoyl-5-(2-Hydroxy-5-(Phenyldiazenyl)Benzylidene)-4-Oxothiazolidin-2-Ylidene)Amino)Benzoic (9a Yellow crystals; yield 62.3%; m.p=256-258° C.; IR (KBr, cm$^{-1}$): 1709(C=O, Thiazole ring); 1719(C=O, carboxylic group); $^1$H NMR (DMSO-d$_6$): δ=6.63 (d, 2H, J=8.6 Hz, Ar), 77.16-7.62 (m, 13H, Ar), 7.93 (s, 1H, Ar), 8.19 (d, 2H, J=8.4 Hz, Ar), 10.38 (s, 1H, OH, exchangeable D$_2$O), 11.14 (s, 1H, COOH, exchangeable D$_2$O); MS: MS: m/z (%)=548 (M$^+$, 6.5), 105 (66.7), 77 (26.6), Anal. Calcd. for C$_{30}$H$_{20}$N$_4$O$_5$S (548.57): C65.49; H, 3.58; N, 10.00; S, 5.64. Found: C65.68; H, 3.67; N, 10.21; S, 5.84%.

Example 19

Characterization of 4-(-3-Benzoyl-5-2-Hydroxy-5-((4-Methoxyphenyl)Diazenyl)Benzylidene)-4-Oxothiazolidin-2-Ylidene)Amino)Benzoic Acid (9b Yellow crystals; yield 81.5%; m.p=266-268° C.; IR (KBr, cm$^{-1}$): 1711(C=O, Thiazole ring); 1718(C=O, carboxylic group); $^1$H NMR (DMSO-d$_6$): δ=3.84 (s, 3H, CH$_3$), 7.08 (d, 1H, J=8.4 Hz, Ar), 7.15-7.98 (m, 13H, Ar), 8.02 (d, 2H, 1=6.6, Ar), 8.12 (s, 1H, Ar), 10.36 (s, 1H, OH, exchangeable D$_2$O), 12.81 (s, 1H, COOH, exchangeable D$_2$O); $^{13}$C NMR (DMSO-d$_6$): δ=56.0, 115.0, 118.7, 122.0, 124.7, 129.9, 131.2, 145.2, 146.5, 162.1, 164.5, 167.3, 169.1, 171.2, 172.5, 1912; MS: MS: m/z (%)=578 (M$^+$, 9.3), 105 (68.7), 77 (49.6), Anal. Calcd. for $C_{31}H_{22}N_4O_6S$ (578.60): C, 64.29; H, 3.73; N, 9.89; S, 5.64. Found: C64.35; H, 3.83; N, 9.68; S, 5.54%.

Example 20

Characterization of 4-(3-Benzoyl-5-(5-(4-Chlorophenyl)Diazenyl)-2-Hydroxybenzylidene)-4-Oxothiazolidin-2-Ylidene)Amino)Benzoic Acid (9c Yellow crystals; yield 67.1%; m.p=260-262° C.; IR (KBr, cm$^{-1}$): 1709(C═O, Thiazole ring); 1717(C═O, carboxylic group); $^1$H NMR (DMSO-d$_6$): δ=6.96 (d, 111, Ar), 7.43-7.98 (m, 12H, Ar), 7.99 (s, 1H, Ar), 8.11 (s, 1H, Ar), 10.32 (s, 1H, OH, exchangeable D$_2$O), 12.79 (s, 1H, COOH, exchangeable D$_2$O); MS: MS: m/z (%)=582 (M$^+$−1, 0.5), 551(1.1), 379(41.6), 240(39.9), 195(57.5), 105 (49.6), 77 (49.6), Anal. Calcd. for $C_{30}H_{19}ClN_4O_5S$ (582.08): C61.80; H, 3.28; N, 9.61; S, 5.50. Found: C, 61.80; H, 3.28; N, 9.61; S, 5.50.% (PCl arylidene of azo salisaldehyde)

Example 21

General Procedure for the Synthesis of 4-(3-Benzoyl-5-((Dimethylamino)Methyl-Ene)-4-Oxothiazolidin-2-Ylidene)Amino)Benzoic Acid (10

4-thiazolidinone (5 mmol) and 10 mL dimethylformamide dimethyl acetal (DMF-DMA) were mixed and heated under reflux for 3 hours without solvent. After cooling, the solid that formed was separated, filtered, and washed with commercial ethanol and recrystallized from 1,4-dioxane.

Characterization of compound 10: Orange crystals; yield 69.5%; m.p=220-222° C.; IR (KBr, cm$^{-1}$): 1726 (C═O, Thiazole ring); 1738(C═O, carboxylic group); $^1$H NMR (DMSO-d$_6$): δ=3.15 (s, 3H, CH$_3$), 6.22 (s, 1H, Ar), 7.44 (d, 2H, 1=7.8 Hz, Ar) 7.55-7.65 (m, 6H, Ar), 7.98 (d, 2H, J=8.2 Hz Ar), 8.14 (d, 2H, J=8.4 Hz, Ar), 11.79 (s, 1H, COOH, exchangeable D$_2$O); MS: MS: m/z (%)=395(M$^+$, 24.4), 105 (66.7), 77 (26.6), Anal. Calcd. for $C_{20}H_{17}N_3O_4S$ (395.43): C60.58; H, 4.13; N, 10.40; S, 8.25. Found: C60.75; H, 4.33; N, 10.63; S, 8.11%.

Example 22

General Procedure for the Synthesis of 4-(5-(((1H-1,2,4-Triazol-3-Yl)Amino) Methylene)-3-Benzoyl-4-Oxothiazolidin-2-Ylidene)Amino)Benzoic Acid (11

Enaminone 10 (5 mmol) and 1H-1,2,4-triazol-3-amine (5 mmol) were mixed in 20 ml of glacial acetic acid. The mixture was refluxed for 5 hours. After cooling, the formed solid was separated and washed with commercial ethanol and recrystallized from DMF.

Pharmacological Activity

Example 23

Antiproliferative Properties

An MU growth assay was utilized for evaluation of the antiproliferative activities of the synthetic thiazolidinones (Table 1) against HCT-116 (colon), MCF7 (breast), and PC3 (prostate) carcinoma cell lines using 5-fluorouracil as a positive control (an approved drug against colon, breast, and skin cancers). It is observed from the data shown in Table 1 that four compounds (6d, 9c, 10, 11) of the synthetic thiazolidine derivatives are potentially promising antiproliferative hits, especially against colon cancer and exhibit higher potency against colon cancer relative to the standard reference (5-fluorouracil) with variable potency (IC$_{50}$ values). It is noteworthy that most of these compounds belong to the thiazolidine library. In comparison, the antiproliferative activities of the same synthetic derivatives (5, 13, 14, 15) against MCF7 cell line (breast cancer) did not exhibit improved cytotoxicities over the standard reference used; however, they were still exhibiting higher potency against breast cancer in low IC$_{50}$ values range from 11.74 to 38.04 μM. Two compounds only from the newly synthesized derivatives (10 and 11) were revealed promising antiproliferative properties against PC3 cell line (prostate cancer) with IC 50 values 67.39 and 98.48 μM respectively.

TABLE 1

| | | IC50 (μM) | | |
|---|---|---|---|---|
| Entry | Compd. | HCT116 | MCF7 | PC3 |
| 1 | 4 | >100.00 | >100.00 | >100.00 |
| 2 | 6a | >100.00 | >100.00 | >100.00 |
| 3 | 6b | >100.00 | >100.00 | >100.00 |
| 4 | 6c | >100.00 | >100.00 | >100.00 |
| 5 | 6d | 12.39 | 34.35 | >100.00 |
| 6 | 6e | >100.00 | >100.00 | >100.00 |
| 7 | 6f | >100.00 | >100.00 | >100.00 |
| 8 | 6g | >100.00 | >100.00 | >100.00 |
| 9 | 6h | >100.00 | >100.00 | >100.00 |
| 10 | 6i | >100.00 | >100.00 | >100.00 |
| 11 | 9a | >100.00 | >100.00 | >100.00 |
| 12 | 9b | >100.00 | >100.00 | >100.00 |
| 13 | 9c | 19.57 | 38.04 | >100.00 |
| 14 | 10 | 12.17 | 17.39 | 67.39 |
| 15 | 11 | 7.17 | 11.74 | 98.48 |
| 16 | 5-fluorouracil | 20.43 | 3.15 | Not Tested |

All the synthesized thiazolidines/thiazolidinones were tested against a normal (non-cancer) cell line (RPE1, retinal pigment epithelial). The observed data can explain and support the safety profile against normal cells. From the results observed, it has been noticed that most of the effective antiproliferative agents synthesized reveal safe cytotoxicity profile against normal cell line tested (high IC$_{50}$ values relative to that of the cancer cell lines tested).

Example 24

EGFR Inhibition Assay

Compounds (6d, 9c, 10 and 11), which showed good antiproliferative activity against HCT-116, MCF7, and PC3 cancer cell lines, were selected to evaluate their inhibitory activity against EGFR using the Alpha Screen system (PerkinElmer, USA), in comparison to the clinically used Gefitinib as standard EGFR inhibitor. The results are reported as a 50% inhibition concentration value (IC$_{50}$) and are summarized in Table 2. The tested compounds exhibited excellent to good inhibitory activity against EGFR with IC$_{50}$ values ranging from 67.44 to 168.44 nM. 4-chlorophenyl-diazenyl-2-hydroxybenzylidene compound 10 exhibited the most pronounced activity of IC$_{50}$; 67.44 nM, comparable to that of the reference drug of IC$_{50}$; 54.21 nM. In the light of the obtained results, replacing the 4-Cl substituent in compound 14 (IC$_{50}$=67.44±1.4 nM) with the 4-methoxy extension in compound 11 ($IC_{50}$=73.92±1.6 nM) resulted in decrease in inhibitory activity against EGFR. Moreover, the unsubstituted phenyldiazenyl-2-hydroxybenzylidene derivatives 9c ($IC_{50}$=168.44±3.6) or 2,4 dihydroxybenzylidene derivative 6d (134.10±2.9 nM) were less potent EGFR inhibitors than the phenyldiazenyl-2-hydroxybenzylidene counterpart 10 and 11. Compounds 10 and 11 represented the highest potency against EGFR, they also showed the highest anti-proliferative activity against HCT-116, MCF7, and PC3 cell lines among the tested derivatives (table 2).

TABLE 2

| ser | Compound code | MW(g/mol) | Results EGFR IC50 (nM) |
|---|---|---|---|
| 1 | 6d | | 134.10 ± 2.9 |
| 2 | 9c | 548.57 | 168.44 ± 3.6 |
| 3 | 10 | 583.01 | 67.44 ± 1.4 |
| 4 | 11 | 578.59 | 73.92 ± 1.6 |
| * | Gefitinib | 446.902 | 54.21 ± 1.1 |

Example 25

Cell Cycle Analysis and Apoptosis Assay

The most effective EGFR inhibiting and high anti-proliferative activity candidate 10 was subjected to cell cycle analysis and apoptotic assay.

Typical neoplastic cells evade apoptosis since accumulation of mutations block apoptosis pathways. It was confirmed that the induction of apoptosis upon effective cancer treatment. It is an important regulatory mechanism in cell growth, maturation and death and is associated with a variety of human diseases, including tumors. Chemotherapy agents may lead to an autophagic response, which is one possible method of inducing apoptosis. There is a unique association between autophagy and apoptosis. While chemotherapeutic drugs induce autophagy, cell cycle arrest and cell senescence, it is imperative the induction of apoptosis and permanent removal of neoplastic cells for effective cancer treatment. Studies on the effect of compound 10 on cell cycle development and induction of apoptosis in cancer MCF7 cells was carried out. The cancer cells were incubated with the compound 14 at its $IC_{50}$ concentration 12.17 µM for 24 hours. The cells were analyzed by flow cytometry technique. Investigation of the resultant data (FIG. 3) revealed a high percentage of cell accumulation of 26.15% at pre G1 phase in MCF7 cells treated with the tested derivative after 24 hours incubation vs 1.29% of the untreated MCF7 cells, indicating cell cycle arrest at G1/S phase.

TABLE 3

| | Sample data | | Results | | | | |
|---|---|---|---|---|---|---|---|
| ser | Sample code | conc uM | % G0-G1 | % S | % G2/M | % Pre-G1 | Comment |
| 1 | Compound 10/MCF7 | | 38.71 | 32.44 | 28.85 | 26.15 | PreG1apoptosis&Cell growtharrest@G2/M |
| 2 | controlMCF7 | | 55.16 | 41.36 | 3.48 | 1.29 | |

Apoptosis Assay

Cell cycle assay of MCF7 cancer cells treated with compound 10 showed the appearance of pre-G1 peak which emphasized the induction of apoptosis. To prove the potency of compound 10 to induce apoptosis, the cells were stained with Annexin V/PI, incubated for 24 h and analyzed. It has been detected that the early and late apoptosis produced by the examined compound 10 certainly indicated its capability to induce significant levels of apoptosis with necrosis percent 3.14. Also, the percentage of late apoptosis (16.6%) induced by compound 10 was higher than that of the early apoptosis (6.41%) which making recovery of apoptotic cells to be healthy is more difficult.

TABLE 4

| | | conc. | Apoptosis | | | |
|---|---|---|---|---|---|---|
| | | ug/ml | Total | Early | Late | Necrosis |
| 1 | Compound 11/MCF7 | | 26.15 | 6.41 | 16.6 | 3.14 |
| 2 | Control MCF7 | | 1.29 | 0.66 | 0.21 | 0.42 |

It is to be understood that the novel arylidene-4-thiazolidinone conjugates are not limited to the specific embodiments described above, but encompasses any and all embodiments within the scope of the generic language of the following claims enabled by the embodiments described herein, or otherwise shown in the drawings or described above in terms sufficient to enable one of ordinary skill in the art to make and use the claimed subject matter.

We claim:

1. A compound having the formula I:

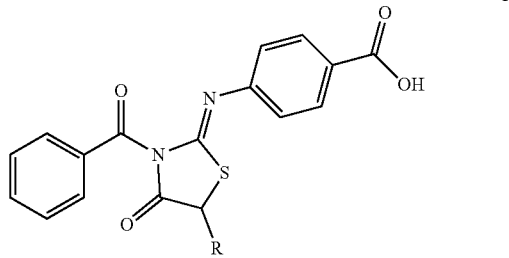

or a pharmaceutically acceptable salt, ester, stereoisomer, or solvate thereof, wherein:

R is selected from the group consisting of hydrogen, 2-hydroxy-5-((E)-phenyldiazenyl)benzylidene, 2-hydroxy-5((4-methoxyphenyl)diazinyl)benzylidene, (dimethylamino)methylene, and an optionally substituted CHAr substituted with one or more substituents independently selected from the group consisting of hydrogen, hydroxy, methoxy, a halogen, naphthalene, a 1H-indol-3-yl, and dimethyl amino; 5-((4-chlorophenyl)-2-hydroxybenzylidene); and (dimethylamino)methylene.

2. The compound of claim 1, wherein R is a hydrogen.
3. The compound of claim 1, wherein R is a —CHphenyl substituted with one or more substituents independently selected from the group consisting of one or more hydroxy groups, one or more methoxy groups, one or more halogens, a naphthalene group, a 1H-indol-3-yl, and a dimethyl amino.
4. The compound of claim 1, wherein R is selected from the group consisting of 2-hydroxy-5-((E)-phenyldiazenyl) benzylidene; 2-hydroxy-5((4-methoxyphenyl)diazinyl)benzylidene; and 5-((4-chlorophenyl)-2-hydroxybenzylidene).
5. The compound of claim 1, wherein the compound is selected from the group consisting of:
   4-((3-benzoyl-4-oxothiazolidin-2-ylidene)amino)benzoic acid (4);
   4-((3-benzoyl-5-(benzylidene)-4-oxothiazolidin-2-ylidene)amino)benzoic acid (6a);
   4-((3-benzoyl-5-(4-hydroxybenzylidene)-4-oxothiazolidin-2-ylidene)amino)benzoic acid (6b);
   4-((3-benzoyl-5-(2,4-dihydroxybenzylidene)-4-oxothiazolidin-2-ylidene) amino) benzoic acid (6c);
   4-((3-benzoyl-5-(4-methoxybenzylidene)-4-oxothiazolidin-2-ylidene)amino) benzoic acid (6d);
   4-((3-benzoyl-5-(3,5-dimethoxybenzylidene)-4-oxothiazolidin-2-ylidene)amino) benzoic acid (6e);
   4-((3-benzoyl-5-(3,5-dichlorobenzylidene)-4-oxothiazolidin-2-ylidene)amino) benzoic acid (6f);
   4-((3-benzoyl-5-(naphthalen-2-ylmethylene)-4-oxothiazolidin-2-ylidene)amino) benzoic acid (6g);
   4-((5-((1H-indol-3-yl)methylene)-3-benzoyl-4-oxothiazolidin-2-ylidene)amino) benzoic acid (6h);
   4-((3-benzoyl-5-(4-(dimethylamino)benzylidene)-4-oxothiazolidin-2-ylidene)amino) benzoic acid (6i);
   4((3-benzoyl-5-(2-hydroxy-5-((E)-phenyldiazenyl)benzylidene)-4-oxothiazolidin-2-ylidene)amino) benzoic acid (9a);
   4-((3-benzoyl-5-(2-hydroxy-5-((4-methoxyphenyl)diazenyl)benzylidene)-4oxothiazolidin-2-ylidene)amino) benzoic acid (9b);
   4-((3-benzoyl-5-(5-((4-chlorophenyl)diazenyl)-2-hydroxybenzylidene)-4oxothiazolidin-2-ylidene)amino) benzoic acid (9c);
   4-((3-benzoyl-5-((dimethylamino)methylene)-4-oxothiazolidin-2-ylidene)amino) benzoic acid (10);
   4-(5-(((1H-1,2,4-triazol-3-yl)amino) methylene)-3-benzoyl-4-oxothiazolidin-2-ylidene)amino)benzoic acid (11); and
   a pharmaceutically acceptable salt, ester, stereoisomer, or solvate thereof.
6. A pharmaceutically acceptable composition comprising a therapeutically effective amount of the compound of claim 1 and a pharmaceutically acceptable carrier.
7. The pharmaceutically acceptable composition of claim 6, wherein the pharmaceutical composition comprises the compound encapsulated in a nanostructure lipid carrier and chitosan core shell.
8. A method of inhibiting epidermal growth factor receptor (EGFR) in a patient, comprising administering to a patient in need thereof a therapeutically effective amount of the compound of claim 1.
9. A method of treating a cancer in a patient, comprising administering to a patient in need thereof a therapeutically effective amount of the compound of claim 1.
10. The method of claim 9, wherein the cancer is one or more selected from the group consisting of colon cancer, prostate cancer, and breast cancer.
11. The method of claim 10, wherein the cancer is colon cancer.

12. A compound having the formula I:

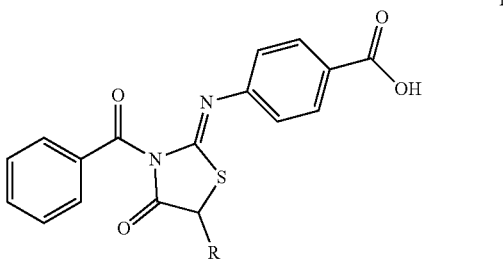

or a pharmaceutically acceptable salt, ester, stereoisomer, or solvate thereof, wherein:
   R is selected from the group consisting of a hydrogen, 2-hydroxy-5-((E)phenyldiazenyl) benzylidene, 2-hydroxy-5((4-methoxyphenyl)diazinyl)benzylidene, 5-((4 chlorophenyl)-2-hydroxybenzylidene), (dimethylamino) methylene, and a —CHphenyl substituted with one or more substituents independently selected from the group consisting of hydrogen, hydroxy, methoxy, chlorine, naphthalene, 1H-indol-3-yl, and dimethyl amino.
13. A pharmaceutically acceptable composition comprising a therapeutically effective amount of the compound of claim 12 and a pharmaceutically acceptable carrier.
14. The pharmaceutically acceptable composition of claim 13, wherein the pharmaceutical composition comprises the compound encapsulated in a nanostructure lipid carrier and chitosan core shell.
15. A method of treating a cancer in a patient, comprising administering to a patient in need thereof a therapeutically effective amount of the compound of claim 12.
16. A compound selected from the group consisting of:
   4-((3-benzoyl-4-oxothiazolidin-2-ylidene)amino)benzoic acid (4);
   4-((3-benzoyl-5-(benzylidene)-4-oxothiazolidin-2-ylidene)amino)benzoic acid (6a);
   4-((3-benzoyl-5-(4-hydroxybenzylidene)-4-oxothiazolidin-2-ylidene)amino)benzoic acid (6b);
   4-((3-benzoyl-5-(2,4-dihydroxybenzylidene)-4-oxothiazolidin-2-ylidene) amino) benzoic acid (6c);
   4-((3-benzoyl-5-(4-methoxybenzylidene)-4-oxothiazolidin-2-ylidene)amino) benzoic acid (6d);
   4((3-benzoyl-5-(3,5-dimethoxybenzylidene)-4-oxothiazolidin-2-ylidene)amino) benzoic acid (6e);
   4-((3-benzoyl-5-(3,5-dichlorobenzylidene)-4-oxothiazolidin-2-ylidene)amino) benzoic acid (6f);
   4-((3-benzoyl-5-(naphthalen-2-ylmethylene)-4-oxothiazolidin-2-ylidene)amino) benzoic acid (6g);
   4-((5-((1H-indol-3-yl)methylene)-3-benzoyl-4-oxothiazolidin-2-ylidene)amino) benzoic acid (6h);
   4-((3-benzoyl-5-(4-(dimethylamino)benzylidene)-4-oxothiazolidin-2-ylidene)amino) benzoic acid (6i);
   4-((3-benzoyl-5-(2-hydroxy-5-((E)-phenyldiazenyl)benzylidene)-4-oxothiazolidin-2-ylidene)amino) benzoic acid (9a);
   4-((3-benzoyl-5-(2-hydroxy-5-((4-methoxyphenyl)diazenyl)benzylidene)-4oxothiazolidin-2-ylidene)amino) benzoic acid (9b);
   4-((3-benzoyl-5-(5-((4-chlorophenyl)diazenyl)-2-hydroxybenzylidene)-4oxothiazolidin-2-ylidene)amino) benzoic acid (9c);

4-((3-benzoyl-5-((dimethylamino)methylene)-4-oxothiazolidin-2-ylidene)amino) benzoic acid (10);

4-(5-(((1H-1,2,4-triazol-3-yl)amino) methylene)-3-benzoyl-4-oxothiazolidin-2-ylidene)amino)benzoic acid (11); and a pharmaceutically acceptable salt, ester, stereoisomer, or solvate thereof.

17. A pharmaceutically acceptable composition comprising a therapeutically effective amount of the compound of claim 16 and a pharmaceutically acceptable carrier.

18. The pharmaceutically acceptable composition of claim 17, wherein the pharmaceutical composition comprises the compound encapsulated in a nanostructure lipid carrier and chitosan core shell.

19. A method of treating a cancer in a patient, comprising administering to a patient in need thereof a therapeutically effective amount of the compound of claim 16.

* * * * *